US012697450B2

(12) United States Patent
Phillips et al.

(10) Patent No.: US 12,697,450 B2
(45) Date of Patent: Aug. 4, 2026

(54) WIRED CONNECTIONS FOR SMART BREATHING CIRCUITS

(71) Applicant: Covidien LP, Mansfield, MA (US)

(72) Inventors: Matthew J. Phillips, Carlsbad, CA (US); Gabriel Sanchez, Valley Center, CA (US); Robert F Frechette, Carlsbad, CA (US)

(73) Assignee: Covidien LP, Mansfield, MA (US)

( * ) Notice: Subject to any disclaimer, the term of this patent is extended or adjusted under 35 U.S.C. 154(b) by 936 days.

(21) Appl. No.: 17/823,283

(22) Filed: Aug. 30, 2022

(65) Prior Publication Data

US 2023/0109332 A1     Apr. 6, 2023

Related U.S. Application Data

(60) Provisional application No. 63/250,779, filed on Sep. 30, 2021.

(51) Int. Cl.
*A61M 16/00*     (2006.01)
*G01R 31/54*     (2020.01)

(52) U.S. Cl.
CPC ...... *A61M 16/024* (2017.08); *A61M 16/0051* (2013.01); *G01R 31/54* (2020.01);
(Continued)

(58) Field of Classification Search
CPC .............. A61M 16/161; A61M 16/024; A61M 16/0816; A61M 16/0875; A61M 16/1095;
(Continued)

(56) References Cited

U.S. PATENT DOCUMENTS 6,874,502 B1 * 4/2005 Nashed ............. A61M 16/0833
128/204.22
8,210,173 B2 7/2012 Vandine
(Continued)

FOREIGN PATENT DOCUMENTS

EP        2 055 337 A1     5/2009
WO      2020261210 A1     12/2020

OTHER PUBLICATIONS

International Search Report for International Application No. PCT/IB2022/059142 mailed Jan. 4, 2023 (15 pages).

*Primary Examiner* — Margaret M Luarca

(57) ABSTRACT

A ventilation system that includes a pressure source, a pneumatic path configured to receive gas from the pressure source and comprising a first pneumatic component coupled to a second pneumatic component. The first pneumatic component includes a first electrical conductor including a first electrical component having a first electrical characteristic. The second pneumatic component comprises a second electrical conductor including a second electrical component having a second electrical characteristic. The first electrical conductor is electrically connected with the second electrical conductor in an electric path. The system performs operations including determining a continuity of the electrical path; displaying a notification regarding the continuity of the electrical path; detecting the unique electrical characteristic of the electric path; and determining a pneumatic characteristic of the pneumatic path.

16 Claims, 13 Drawing Sheets

(52) U.S. Cl.
CPC . *A61M 2202/02* (2013.01); *A61M 2205/3327* (2013.01); *A61M 2205/702* (2013.01)

(58) Field of Classification Search
CPC .............. A61M 16/16; A61M 16/0833; A61M 2205/6027; A61M 2205/14; A61M 2205/3317
See application file for complete search history.

(56) References Cited

U.S. PATENT DOCUMENTS

| | | |
|---|---|---|
| 2010/0094366 A1 | 4/2010 | McCarthy |
| 2010/0256476 A1* | 10/2010 | Wood ................ A61M 16/0488 128/207.14 |
| 2011/0023874 A1* | 2/2011 | Bath ................ A61M 16/1075 128/203.14 |
| 2012/0285468 A1* | 11/2012 | Birch ................... A61M 16/10 128/206.24 |
| 2014/0094366 A1 | 4/2014 | Mann et al. |
| 2014/0216459 A1 | 8/2014 | Vos et al. |
| 2019/0076617 A1* | 3/2019 | Smith ................ A61M 16/161 |
| 2020/0121873 A1* | 4/2020 | Hudson ................. G16H 20/40 |
| 2020/0330717 A1 | 10/2020 | Doudkine et al. |

\* cited by examiner

Example Lookup Table For Conversion of Electrical Characteristics to Pneumatic Characteristics

| Impedance | Pneumatic Resistance | Pneumatic Compliance |
|-----------|---------------------|----------------------|
| Z1 | PR1 | PC1 |
| Z2 | PR2 | PC2 |
| Z3 | PR3 | PC3 |
| ... | ... | ... |
| Zn | PRn | PCn |

FIG. 6A

Example Lookup Table For Conversion of Electrical Characteristics to Pneumatic Component Identification

| Impedance | Pneumatic ID |
|-----------|--------------|
| Z1 | PID1 |
| Z2 | PID2 |
| Z3 | PID3 |
| ... | ... |
| Zn | PIDn |

FIG. 6B

| Example Lookup Table For Conversion of Electrical Characteristics to Pneumatic Characteristics | | | | |
|---|---|---|---|---|
| Resistance | Pneumatic Resistance | | Electrical Capacitance | Pneumatic Compliance |
| R1 | PR1 | | C1 | PC1 |
| R2 | PR2 | | C2 | PC2 |
| R3 | PR3 | | C3 | PC3 |
| ... | ... | | ... | ... |
| Rn | PRn | | Cn | PCn |

DETERMINE CONTINUITY OF ELECTRICAL PATH

1102

DISPLAY NOTIFICATION REGARDING CONTINUITY OF ELECTRICAL PATH

1104

DETECT UNIQUE ELECTRICAL CHARACTERISTIC OF THE ELECTRICAL PATH

1106

BASED ON UNIQUE ELECTRICAL CHARACTERISTIC, IDENTIFY PNEUMATIC COMPONENTS AND/OR ELECTRICAL COMPONENTS

1108

DETERMINE PNEUMATIC CHARACTERISTIC OF PNEUMATIC PATH

1110

WIRED CONNECTIONS FOR SMART BREATHING CIRCUITS

CROSS-REFERENCE TO RELATED APPLICATIONS

This application claims the benefit of U.S. Provisional Application No. 63/250,779 filed Sep. 30, 2021, entitled "Wired Connections for Smart Breathing Circuits," which is incorporated herein by reference in its entirety.

INTRODUCTION

Medical ventilator systems have long been used to provide ventilatory and supplemental oxygen support to patients. These ventilators typically comprise a connection for pressurized gas (air, oxygen) that is delivered to the patient through a conduit or tubing. As each patient may require a different ventilation strategy, modern ventilators may be customized for the particular needs of an individual patient. For example, based on the patient characteristics and the characteristics of breathing conduits and tubing, different ventilation strategies may be utilized.

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

In an aspect, the technology relates to a ventilation system that includes a pressure source and a pneumatic path configured to receive gas from the pressure source. The pneumatic path includes a first pneumatic component coupled to a second pneumatic component. The first pneumatic component includes a first electrical conductor including a first electrical component having a first electrical characteristic. The second pneumatic component comprises a second electrical conductor including a second electrical component having a second electrical characteristic different than the first electrical characteristic. The first electrical conductor is electrically connected with the second electrical conductor in an electric path, and the first and second electrical characteristics produce a unique electrical characteristic of the electric path. The ventilation system also includes a processor and memory storing instructions that, when executed by the processor, causes the ventilation system to perform operations. The operations include determining a continuity of the electrical path; displaying a notification regarding the continuity of the electrical path; detecting the unique electrical characteristic of the electric path; based on the unique electrical characteristic, identifying at least one of the first and second pneumatic components or the first and second electrical components; and based on the identifying, determining a pneumatic characteristic of the pneumatic path.

In an example, the pneumatic characteristic includes at least one of airway resistance and airway compliance. In another example, the pneumatic characteristic includes at least one of a gas volume or gas flow alteration caused by the at least one of the first pneumatic component or the second pneumatic component. In yet another example, the first pneumatic component is one of a breathing circuit, an inspiratory filter, an expiratory filter, a humidification system, a wye, a flow sensor, an endotracheal tube, a nasal cannula, a mask, a suction catheter, a water trap, a nebulizer, or a percussor; and the second pneumatic component is one of a breathing circuit, an inspiratory filter, an expiratory filter, a humidification system, a wye, a flow sensor, an endotracheal tube, a nasal cannula, a mask, a suction catheter, a water trap, a nebulizer, or a percussor. In still another example, the first electrical characteristic is at least one of electrical impedance, electrical resistance, electrical capacitance, or electrical inductance; and the pneumatic characteristic is determined based on the electrical characteristic. In a further example, determining the continuity of the electrical path includes emitting, through the electrical path, an interrogation signal that includes a time series of different frequencies; and detecting a response signal that includes a response to different frequencies of the interrogation signal.

In another example, determining the continuity of the electrical path includes emitting, through the electrical path, an interrogation signal that is a direct current (DC) voltage, and the unique electrical characteristic is an electrical resistance. In yet another example, the operations further include adjusting a ventilation parameter according to the pneumatic characteristic, wherein the ventilation parameter is at least one of flow, pressure, volume; and delivering ventilation according to the adjusted ventilation parameters. In still another example, determining the continuity of the electrical path includes, detecting a response signal that includes a first identifier for the first pneumatic component and a second identifier for the second pneumatic component, and determining the at least one pneumatic characteristic includes performing a lookup operation to identify the at least one pneumatic characteristic. In still yet another example, the first electrical conductor including the first electrical component is removable from the first pneumatic component. In a further example, the system further includes a third pneumatic component; and an adapter comprising a third electrical conductor including a third electrical component corresponding to the third pneumatic component, the adapter coupling the third pneumatic component with at least one of the first pneumatic component or the second pneumatic component.

In another aspect, the technology relates to a method for automatically characterizing pneumatic components of a pneumatic path for a ventilator. The method includes emitting an interrogation signal through electrical conductors of a plurality of pneumatic components of the pneumatic path; monitoring for a response signal from the electrical conductors of the plurality of pneumatic components of the pneumatic path; and based on the monitoring of the response signal, performing at least one of: displaying a first user interface, on a display of the ventilator, indicating continuity of the pneumatic path has been detected; performing an abbreviated circuit check; displaying a second user interface, on the display of the ventilator, indicating continuity of the pneumatic path has not been detected; or activating a disconnect alarm.

In an example, the method further includes detecting a response signal; and based on the detection of the response signal, performing at least one of displaying the first user interface or performing the abbreviated circuit check. In another example, the method further includes detecting an absence of a response signal; and performing at least one of: displaying the second user interface; or activating the disconnect alarm. In yet another example, the method further includes detecting a response signal, wherein the response signal is based on the interrogation signal as altered by electrical identification circuits of the pneumatic components of the pneumatic path; and based on the response signal, determining at least one pneumatic characteristic of the pneumatic path. In yet another example, the method further includes determining an electrical characteristic of the pneumatic path, wherein the electrical characteristic is at least one of electrical impedance, electrical resistance, electrical capacitance, or electrical inductance; and the at least one pneumatic characteristic is determined based on the electrical characteristic.

In another aspect, the technology relates to a method, performed by a ventilator, for automatically characterizing pneumatic components of a pneumatic path. The method includes emitting an interrogation signal through electrical conductors of a first pneumatic component and a second pneumatic component of a pneumatic path, wherein the interrogation signal is altered by a first electrical identification circuit of the first pneumatic component and a second identification circuit of the second pneumatic component; receiving a response signal in response to the interrogation signal; based on the response signal, determining at least one pneumatic characteristic of the first pneumatic component and the second pneumatic component; and delivering ventilation that is compensated based on the pneumatic characteristics.

In an example, the method further includes determining an electrical characteristic of the first electrical identification circuit, wherein the electrical characteristic is at least one of electrical impedance, electrical resistance, electrical capacitance, or electrical inductance; and the at least one pneumatic characteristic is determined based on the electrical characteristic. In another example, the interrogation signal includes a time series of different frequencies, and the response signal includes a response to different frequencies of the interrogation signal. In yet another example, the response signal includes a first identifier for the first pneumatic component and a second identifier for the second pneumatic component, and determining the at least one pneumatic characteristic includes performing a lookup operation to identify the at least one pneumatic characteristic.

BRIEF DESCRIPTION OF THE DRAWINGS

The following drawing figures, which form a part of this application, are illustrative of aspects of systems and methods described below and are not meant to limit the scope of the disclosure in any manner, which scope shall be based on the claims.

FIG. 6A depicts an example lookup table for conversion of electrical characteristics to pneumatic characteristics.

FIG. 6B depicts an example lookup table for conversion of electrical characteristics to pneumatic characteristics.

FIG. 7 depicts another example lookup table for conversion of electrical characteristics to pneumatic characteristics.

Figure 1A:
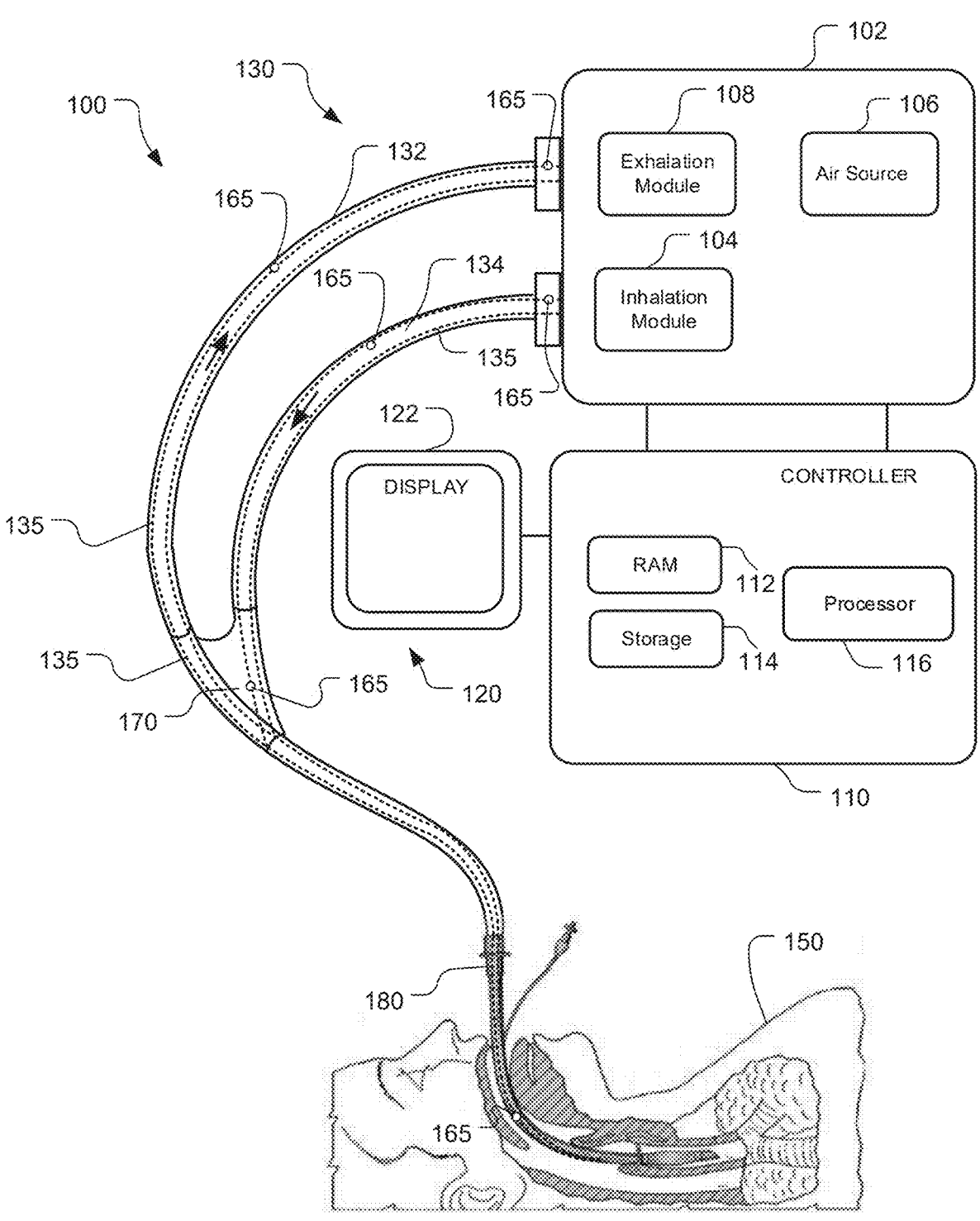
FIG. 1A is a diagram illustrating an example of a medical ventilation system connected to a human patient.

While examples of the disclosure are amenable to various modifications specific aspects have been shown by way of example in the drawings and are described in detail below. The intention is not to limit the scope of the disclosure to the particular aspects described. On the contrary, the disclosure is intended to cover all modifications, equivalents, and alternatives falling within the scope of the disclosure and the appended claims.

DETAILED DESCRIPTION

As discussed briefly above, medical ventilators are used to provide breathing gases to patients who are otherwise unable to breathe sufficiently. Delivery of breathing gases by the ventilator is based on ventilation settings, which are dependent on the needs of the patient and the pneumatic characteristics of the pneumatic components of the breathing circuit. For instance, the airway compliance and airway resistance of the breathing circuit or pneumatic path as a whole, or components thereof, may be used to determine proper ventilation parameters and compensate gas delivery to achieve the desired ventilation settings. Currently, to determine such pneumatic characteristics, a test is executed by the ventilator that allows for a calculation of the pneumatic characteristics. The test delivers varying amounts of gas through the breathing circuit while a patient is not connected, and based on the pressure and flow measurements of the gas, the ventilator is able to determine pneumatic characteristics of the attached breathing circuit. This test may be referred to as a short self test (SST) or circuit check, and one example of such a test is the SST used with the Puritan Bennett™ 980 Series Ventilator. The SST, however, has some drawbacks including that the test may require a substantial amount of time (e.g., multiple minutes), and the patient is not able to be connected to the ventilator during that time. This delay in providing ventilation is undesirable, as the SST is performed whenever a new patient is to be connected to a ventilator or when components of the breathing circuit or pneumatic path are changed, such as a changing a filter, humidification system, nebulizer, flow sensor, water trap, suction catheter, etc. or changing the whole breathing circuit all together.

Among other things, the present technology is able to alleviate the above issues by automatically determining pneumatic characteristics of the breathing circuit or pneumatic path based on electrical signals passed through the pneumatic components of the breathing circuit. Accordingly, the pneumatic tests (e.g., SSTs) that have been previously used to determine pneumatic characteristics may be eliminated or significantly reduced. More specifically, with the present technology, the pneumatic components of the breathing circuit or pneumatic path may include electrical conductors and electrical identification circuits. The ventilator may emit an interrogation signal that is passed through the conductors and electrical identification circuits to ultimately result in a response signal that is detected by the ventilator. Based on the response signal, the ventilator determines pneumatic characteristics for the pneumatic components of the breathing circuit.

The determination of the pneumatic characteristics may be based on an electrical characteristic (e.g., electrical resistance, impedance, capacitance, inductance) of the electrical identification circuits. For instance, the electrical identification circuits may include minimal electrical components, such as a resistor, capacitor, and/or inductor, and the total electrical effect of the combined electrical identification circuits may result in a composite or aggregate electrical characteristic or characteristics that can be used to determine one or more pneumatic characteristics of the breathing circuit. In other examples, the response signal may include data from the electrical identification circuits that identifies one or more pneumatic components in the breathing circuit. Additionally or alternatively, the data from the electrical identification circuits may also include the actual values for the pneumatic characteristics. The present technology also provides the advantage of being able to detect a disconnect of pneumatic components based on the continuity of the electrical signals rather than based on (and/or in addition to) analyses of gas flow or pressure.

Figure 1B:
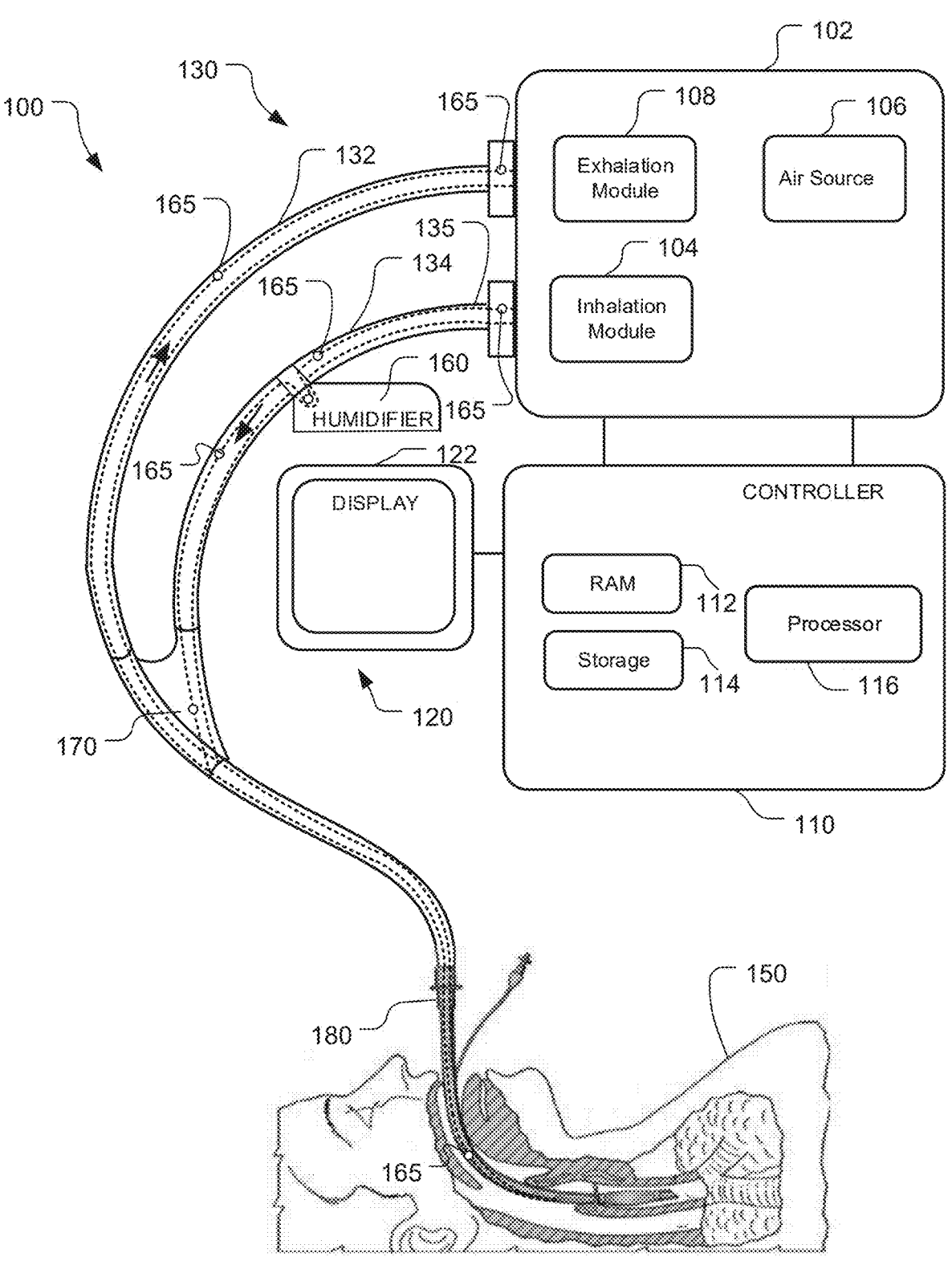
FIG. 1B is a diagram illustrating another example of a medical ventilation system connected to the human patient.

FIGS. 1A-1B are diagrams illustrating examples of a medical ventilation system 100 (e.g., ventilator) connected to a patient 150. The medical ventilation system 100 may provide various forms of ventilation, such as positive pressure ventilation and high flow oxygen therapy, to the patient 150. The medical ventilation system 100 includes a pneumatic system 102 (also referred to as a pressure generating system 102) for circulating breathing gases to and from patient 150 via the breathing circuit 130. The breathing circuit 130 couples the patient 150 to the pneumatic system via a patient interface 180, which may considered part of the breathing circuit 130. The patient interface 180 may be invasive (e.g., endotracheal tube, as shown) or non-invasive (e.g., nasal or oral mask, nasal cannula). The medical ventilation system 100 controls the flow of gases into the breathing circuit 130 by controlling (adjusting, opening, or closing) an inhalation flow valve or blower which may be part of the inhalation module 104. Additionally, a humidifier 160 (shown in FIG. 1B) or humidification system may be placed along the breathing circuit 130 to humidify the breathing gases being delivered to the patient 150. A pressure sensor and flow sensor may be located at or near the inhalation module 104 and/or the exhalation module 108 to measure flow and pressure.

The breathing circuit 130 may be a two-limb circuit (shown) or a one-limb circuit (also called single limb, with an inhalation side only). In a two-limb example, a wye-fitting 170, may be provided to couple the patient interface 180 to an inspiratory or inhalation limb 134 and an expiratory or exhalation limb 132 of the breathing circuit 130.

Pneumatic system 102 may have a variety of configurations. In the present example, system 102 includes an exhalation module 108 coupled with the exhalation limb 132 and an inhalation module 104 coupled with the inhalation limb 134. An air source 106, which may be a compressor, blower, or other source(s) of pressurized gases (e.g., air, oxygen, and/or helium), is coupled with inhalation module 104 to provide breathing gas to the inhalation limb 134. The pneumatic system 102 may include a variety of other components, including mixing modules, valves, sensors, tubing, accumulators, filters, etc., which may be internal or external sensors to the ventilator (and may be communicatively coupled, or capable communicating, with the ventilator).

Controller 110 is operatively coupled with pneumatic system 102, signal measurement and acquisition systems, and a user interface 120. Controller 110 may include hardware memory 112, one or more processors 116, storage 114, and/or other components of the type found in command and control computing devices. In the depicted example, user interface 120 includes a display 122 that may be touch-sensitive and/or voice-activated, enabling the display 122 to serve both as an input and output device to enable a user to interact with the medical ventilation system 100 (e.g., change ventilation settings, select operational modes, view monitored parameters, etc.).

The memory 112 includes non-transitory, computer-readable storage media that stores software that is executed by the processor 116 and which controls the operation of the medical ventilation system 100. For instance, the memory 112 may store instructions that, when executed by the processor 116, causes the ventilation system 100 to perform the operations discussed herein. In an example, the memory 112 includes one or more solid-state storage devices such as flash memory chips. In an alternative example, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid-state memory technology, CD-ROM, DVD, or other optical storage, magnetic cassettes, magnetic tape, magnetic disk storage or other magnetic storage devices, or any other medium which can be used to store the desired information and which can be accessed by the computer.

The pneumatic components of the breathing circuit 130 may each include at least one electrical conductor 135 (indicated by the dashed lines) and an electrical identification circuit 165 (indicated by circles on the dashed lines). The pneumatic components may include any component that affects gas flow through the breathing circuit 130 (e.g., any component that affects gas flow between the pneumatic system 102 and the patient 150). For example, the pneumatic components may include a hose, a tube, an inspiratory filter, an expiratory filter, a humidification chamber, a wye, a flow sensor, an endotracheal tube, a nasal cannula, a mask, a suction catheter, a water trap, a nebulizer, a nitrous oxide device, and/or a percussor, among other possible pneumatic components. The electrical conductors 135 may include wires, traces, or any other physical electrical conductors capable of carrying an electrical signal. For instance, the controller 110 may emit electrical signals onto the electrical conductors 135, and the controller 110 may also read electrical signals from the electrical conductors 135. While two electrical conductors 135 are depicted as being included in the pneumatic components of the breathing circuit 130, in other examples more or fewer electrical conductors 135 may be used. For instance, a single electrical conductor may be used where the electrical conductor 135 is continuous through the breathing circuit 130 (such as from the inspiratory port to the expiratory port). In some examples, the two or more electrical conductors may be used as a transmission path for a signal and a return path for a signal, where the transmission path and the return path are connected to one another in a particular component, such as the wye 170 or the patient interface 180. In such examples, the inspiratory side of breathing circuit 130 (or pneumatic path) and the expiratory side of the breathing circuit 130 (or pneumatic path) may be analyzed separately. For instance, the pneumatic characteristics of one side may be determined separately from the pneumatic characteristics of the other side.

The pneumatic components may also each include an electrical identification circuit 165. The electrical identification circuit 165 may be a singular electrical component, such as a resistor, capacitor, or inductor. In some examples, the electrical identification circuit 165 may include a simple electrical circuit or filter, such as RC filter, LC filter, RLC filter, or similar circuit formed by a small number of circuit components. The electrical identification circuit 165 may be provided in series or in parallel the electrical conductors and other the electrical identification circuits 165. The electrical identification circuit 165 may itself not form a complete "circuit." Rather, the electrical identification circuit may be a singular electrical component and/or a combination of electrical components. The term electrical identification circuit may also be referred to herein as an electrical identifier and/or an electrical identification component.

The electrical characteristics (e.g., electrical resistance, impedance, capacitance, and/or inductance) of the electrical identification circuit 165 are selected to have a relationship to the pneumatic characteristics (e.g., pneumatic or airway resistance, compliance, volume deadspace, etc.) of the pneumatic component for which the electrical identification circuit 165 is a part. Thus, once the electrical characteristics of the electrical identification circuits 165 for the pneumatic components of the breathing circuit 130 are known, the pneumatic characteristics of the breathing circuit 130 may be determined.

The pneumatic characteristics may also include other characteristics that affect pressure or flow of the breathing gases. For example, some pneumatic components, such as a nebulizer or a nitrous-oxide device, may inject additional gas into the breathing circuit. Such gas volume or gas flow alteration caused by a pneumatic component may also be considered a pneumatic characteristic of the pneumatic component.

In other examples, the electrical identification circuit 165 may be a microchip or an integrated circuit that stores data regarding the pneumatic component of which it is a part. For instance, the integrated circuit may store identification information about the particular pneumatic component (such as a part number, serial number, etc.) The integrated circuit may also or alternatively store data representing the pneumatic characteristics (e.g., pneumatic or airway resistance, compliance, etc.) of the particular pneumatic component. For instance, the data may be the values of the pneumatic characteristics.

The electrical conductors 135 of each pneumatic component may be configured such that they can be electrically connected to electrical conductors of another pneumatic component when the two pneumatic components are physically connected together. For example, when the ventilation tubing of the inhalation limb 134 is connected to the wye-fitting 170, the electrical conductors 135 of the ventilation tubing become in contact with the electrical conductors 135 of the wye-fitting 170. Thus, there is electrical continuity and pneumatic continuity between the electrical conductors 135 of the ventilation tubing and the electrical conductors 135 of the wye-fitting 170 when they are properly connected to one another. The path formed by the conductors 135 and the electrical identification circuits 165 when the corresponding pneumatic components are connected may be referred to as an electrical path.

Additional pneumatic components may also be added to the breathing circuit 130 and electrical continuity can be retained. The system can automatically determine the impact on the pneumatic characteristics of the breathing circuit 130 based on the added pneumatic component(s). For example, the breathing circuit 130 depicted in FIG. 1A does not include a humidifier or humidification system 160. A humidification system 160 may be added to the breathing circuit 130 as shown in FIG. 1B. The humidification system 160 may include its own electrical conductors 135 and electrical identification circuit 165. When the humidification system 160 is connected to the breathing circuit 130, the electrical conductors 135 of the humidification system 160 connect to the electrical conductors 135 on the inhalation limb 134 of the breathing circuit 130 to create a continuous electrical path that can carry an electrical signal. As used herein, the combination of pneumatic components (including the tubing of the breathing circuit 130) form a pneumatic path where the pneumatic components affect the flow of gas through the pneumatic path. The pneumatic path may also be referred to as a breath delivery path. In some examples, the pneumatic path may include just the breathing circuit 130 (e.g., inhalation limb, wye, and exhalation limb tubing). In other examples where additional pneumatic components are incorporated, the pneumatic path may also include those additional pneumatic components in addition to the breathing circuit 130.

Each of the pneumatic components may include its own electrical conductors 135 such that when the pneumatic components of the pneumatic path are properly connected, there is also electrical continuity through the entire pneumatic path. In such examples, the ventilator may emit an interrogation signal through the electrical conductors 135 of the pneumatic path and monitor for a response signal to determine if there is electrical connection across the pneumatic path, which may be determined by testing for electrical continuity or detection of a response signal. For instance, the ventilator may apply a voltage difference between the electrical conductor 135 at the inspiratory port and the electrical conductor 135 at the expiratory port. If current flows through the electrical circuit of the pneumatic path, a response signal can be detected at the expiratory port (or inspiratory port depending on the voltage/signal configuration). If there is no electrical continuity through the breathing circuit 130, there may be a disconnected pneumatic component that would result in problems in attempting to deliver breathing gases to the patient 150, or an un-identified pneumatic component (without conductors 135) that needs to be characterized. For instance, an interface (e.g., cannula or tracheal tube) may be have become unintentionally disconnected. The signal generated for determining electrical continuity (which may be a simple direct-current (DC) signal in some implementations) may also be referred to as a continuity signal or integrity signal, which is a type of interrogation signal. For example, applying an electrical voltage to determine a resistance value of a resistor may be considered to be within the scope of emitting an interrogation signal and receiving a response signal.

In addition, the ventilator may emit an interrogation signal through the electrical conductors 135 and the electrical identification circuits 165 of the pneumatic path. As discussed above, emitting the interrogation signal may include applying a constant voltage (e.g., DC voltage) and/or a varying voltage (e.g., custom data signal and/or AC signal) across the electrical conductors 135. Each of the electrical identification circuits 165 affects the signal as the signal passes through the electrical identification circuits 165. As a result, the response signal (e.g., the signal as altered by the electrical identification circuits 165) may be detected and analyzed to determine the electrical characteristics of the electrical identification circuits 165.

As one example, each electrical identification circuit 165 may include a resistor having an electrical resistance corresponding to the pneumatic resistance of the pneumatic component for which the electrical identification circuit 165 is a part. As the interrogation signal passes through the electrical identification circuits 165, the voltage drops and the aggregate or composite electrical resistance of all the electrical identification circuits 165 of the breathing circuit 130 or pneumatic path may be determined. Based on the total electrical resistance, the total pneumatic resistance may be determined as discussed further herein.

In some examples, the pneumatic resistance of the individual pneumatic components may also be determined from the total electric resistance. For instance, as discussed further below, where the electric resistances of the electrical identification circuits 165 are chosen to form unique total electrical resistances, the pneumatic resistances of the individual pneumatic components may be determined. As an example, a first electrical identification circuit 165 for a first pneumatic component may have an electrical resistance of a 1 kiloohms (kΩ), a second electrical identification circuit 165 for a second pneumatic component may have an electrical resistance of a 3 kΩ, and a third electrical identification circuit 165 for a third pneumatic component may have an electrical resistance of a 10 kΩ. In such an example, if the measured total electrical resistance is 4 kΩ, a determination may be made that the first pneumatic component and the second pneumatic component are connected in series. Similarly, if the measured total electrical resistance is 11 kΩ, a determination may be made that the first pneumatic component and the third pneumatic component are connected in series. Likewise, if the measured total electrical resistance is 14 kΩ, a determination may be made that all three pneumatic components are connected in series.

In some examples, the electrical characteristic, such as resistance, may be scaled and grouped based on the type of pneumatic components. For example, electrical identification circuits for breathing circuits (e.g., tubes/hoses) may be provided with resistances in 1 kΩ intervals between 1 kΩ and 50 kΩ. Other pneumatic component types may have different scales and ranges. For instance, electrical identification circuits for humidification systems may be provided with resistances in 10 kΩ intervals between 100 kΩ and 200 kΩ, electrical identification circuits for filters may be provided with resistances in 10 kΩ increments between 300 kΩ to 350 kΩ, and electrical identification circuits for tracheal tubes may be provided with resistances in 10 kΩ intervals between 400 kΩ and 500 kΩ.

While resistance is one example of an electrical characteristic, other electrical characteristics, such as electrical impedance, capacitance, or inductance may be used to determine one or more pneumatic characteristics. The type of electrical characteristic and interrogation signal used may be dependent on the type of circuit used for the electrical identification circuits 165 and the type of interrogation signal used. For instance, if the electrical identification circuits 165 are formed as in-series capacitors, a non-changing DC signal may not be an appropriate signal to use as it would not pass through the capacitors.

As another example, the electrical identification circuits 165 may be formed as circuits that have different effects on different frequencies, such as band-pass filters which allow frequencies in particular bands to pass through the filters. In such an example, the interrogation signal may be provided as a time series of different frequencies. The electrical identification circuits 165 may affect (such as by filtering or modulating) the different frequencies in different manners. Accordingly, the response signal may be analyzed to determine the types of electrical identification circuits 165 (and/or the electrical characteristics thereof) present in the breathing circuit 130 or pneumatic path. For example, one electrical identification circuit 165 (e.g., a band-pass filter) may filter out one frequency, but allow another frequency to pass through. Another electrical identification circuit 165 may then filter and allow different frequencies. By analyzing which frequencies of the interrogation signals are affected by the electrical identification circuit 165, determinations can be made as to which electrical identification circuits 165 are present in the pneumatic path. That information may then be used to determine the pneumatic characteristics of the pneumatic components of the breathing circuit 130 or pneumatic path. For example, reference tables may be generated that correlate the electrical identification circuits 165 with one or more pneumatic characteristics of the corresponding pneumatic component.

Once the pneumatic characteristics are determined in the initial interrogation of the pneumatic path (e.g., at startup), those pneumatic characteristics may be used to determine or control ventilation settings for delivering breathing gases to the patient. For instance, the pneumatic characteristics may include one or more pneumatic resistance values that may be used to generate a pneumatic resistance versus flow curve or table. That values recorded may then be used to compensate gas delivery and monitoring to allow for delivering breathing gases to the patient per the settings.

Figure 2A:
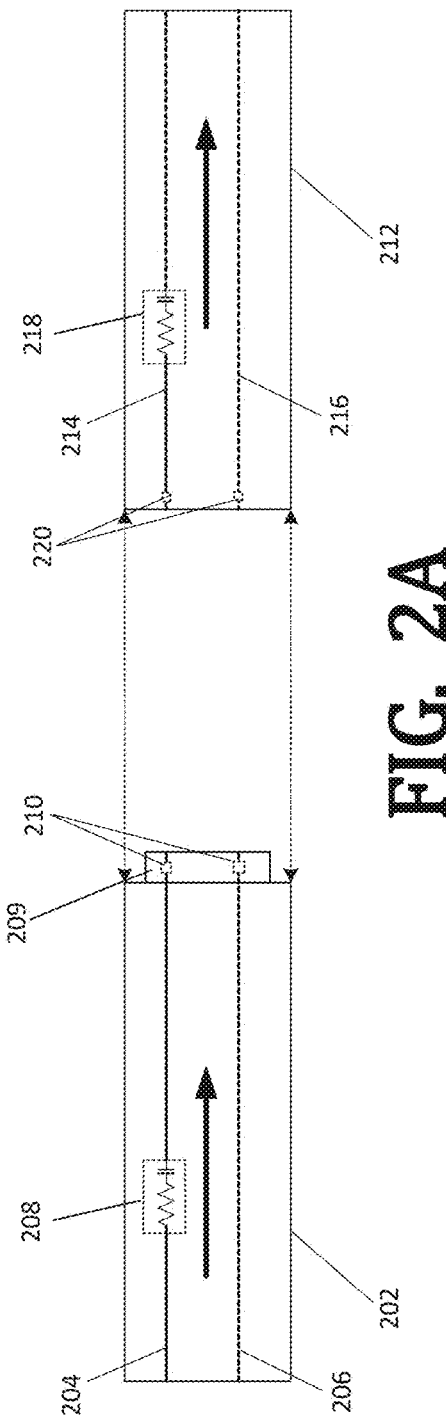
FIG. 2A is a diagram illustrating example pneumatic components including electrical identification circuits.

FIG. 2A is a diagram illustrating example pneumatic components including electrical identification circuits. More specifically, FIG. 2A depicts a first pneumatic component 202 that is to be connected to a second pneumatic component 212. In the example depicted, the first pneumatic component 202 includes a first electrical conductor 204 and a second electrical conductor 206. The first electrical conductor 204 includes a first electrical identification circuit 208. The electrical identification circuit 208 in the first pneumatic component 202 is shown as an RC filter as part of the first electrical conductor 204. In some examples, however, the electrical identification circuit 208 may be a resistor, capacitor, inductor, LC filter, RLC filter, or other type of circuit. The electrical circuit components (e.g., resistors, capacitors, inductors) of the first electrical identification circuit 208 are selected such that they have electrical characteristics that identify the first pneumatic component 202 and/or the pneumatic characteristics of the first pneumatic component 202. In other examples, the first electrical identification circuit 208 may be an integrated circuit storing data about the first pneumatic component 202. For instance, the integrated circuit may store identification information about the first pneumatic component 202 (such as a part number, serial number, etc.) The integrated circuit may also or alternatively store data representing the values of the pneumatic characteristics (e.g., pneumatic or airway resistance, compliance, etc.) of the first pneumatic component 202.

The first pneumatic component 202 includes a mating projection 209 to assist with mating or connecting the first pneumatic component 202 with the second pneumatic component 212. The mating projection 209 may include first mating contacts 210 that are in respective electrical contact with the first electrical conductor 204 and the second electrical conductor 206.

The second pneumatic component 212 includes a first electrical conductor 214 and a second electrical conductor 216. The first electrical conductor 214 includes a second electrical identification circuit 218. The second electrical identification circuit 218 may be the same type of circuit as the first electrical identification circuit 208 (e.g., an RC filter). In other examples, the second electrical identification circuit 218 may be a different type of circuit from the first electrical identification circuit 208. In such examples, the second electrical identification circuit 218 may respond to a different types of interrogation signals in a different manner than the first electrical identification circuit 208, which may allow for further distinction between the first pneumatic component 202 and the second pneumatic component 212. Similar to the first electrical identification circuit 208, however, the components of the second electrical identification circuit 218 are selected such that they identify the second pneumatic component 212 and/or the pneumatic characteristics of the second pneumatic component 212. While the first electrical identification circuit 208 and the second electrical identification circuit 218 are shown in series, they may also be provided in parallel in other examples.

The second pneumatic component 212 includes second mating contacts 220 that may be part of a recess configured to receive the projection 209 of the first pneumatic component 202. When the first pneumatic component 202 is connected to the second pneumatic component 212, the first mating contacts 210 are in contact with the second mating contacts 220 such that the first electrical conductor 204 of the first pneumatic component 202 has electrical continuity with the first electrical conductor 214 of the second pneumatic component 212, and the second electrical conductor 206 of the first pneumatic component 202 has electrical continuity with the second electrical conductor 216 of the second pneumatic component 212. An electrical path is formed including the first electrical conductor 204 of the first pneumatic component 202, the first electrical identification circuit 208, the first electrical conductor 214 of the second pneumatic component 212, and the second electrical identification circuit 218. Thus, electric signals can be passed to and from the first pneumatic component 202 to the second pneumatic component 212 along the electrical path. Gas can also be passed through the first pneumatic component 202 and the second pneumatic component 212 as indicated by the black arrow.

If the first pneumatic component 202 and the second pneumatic component 212 become physically disconnected, the electrical connection between the first pneumatic component 202 and the second pneumatic component 212 is also disconnected. Accordingly, a physical disconnect between the components may be detected electrically. For example, if a signal cannot be passed through the components (e.g., a signal is emitted on one side but not detected on the other side), a determination may be made that there is a physical disconnect between at least two of the pneumatic components in the pneumatic path.

Figure 2B:
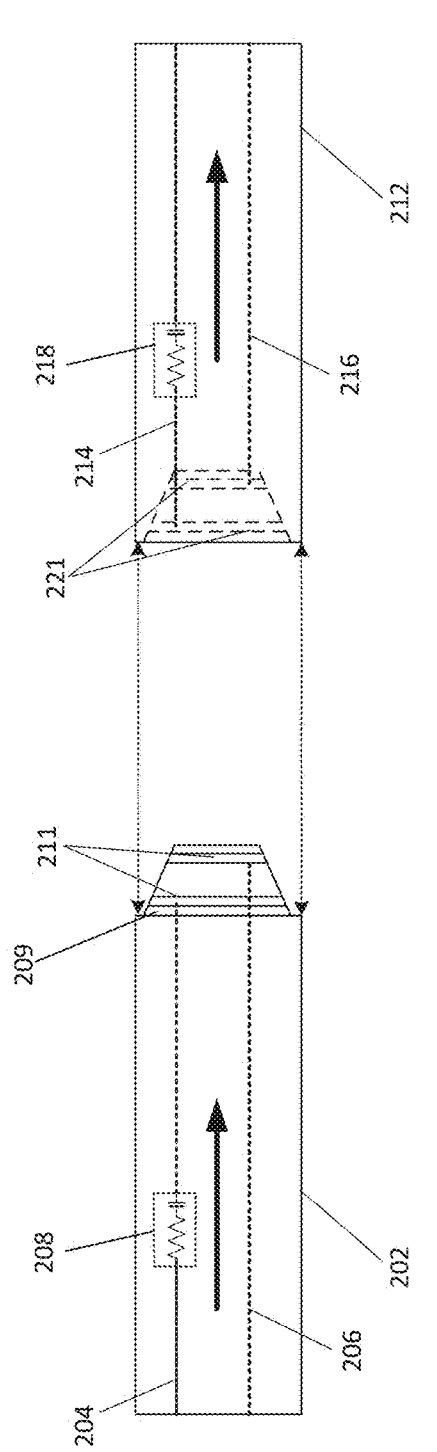
FIG. 2B is a diagram illustrating example pneumatic components including electrical identification circuits.

FIG. 2B is a diagram illustrating example pneumatic components including electrical identification circuits. More specifically, FIG. 2B depicts a first pneumatic component 202 and a second pneumatic component 212 that are substantially the same as the pneumatic components of FIG. 2A with the exception of the mating projection and mating contacts. In the first pneumatic component 202 depicted in FIG. 2B, the mating projection 209 has a frustoconical shape, and the recess of the second pneumatic component 212 has a similarly shaped recess for receiving the mating projection 209. While a frustoconical shape is shown, it should be appreciated other shapes and configurations may be used for mating the pneumatic components.

The first mating contacts 211 and the second mating contacts 221 shown in FIG. 2B are also different from the mating contacts shown in FIG. 2A. The first mating contacts 211 are bands that extend around the circumference of the projection 209. The first mating contacts 211 are spaced apart such that one mating contact is closer to the end of the first pneumatic component 202 than the other mating contact. The second mating contacts 221 are similarly configured such that when the first pneumatic component 202 is connected to the second pneumatic component 212, the first mating contacts 211 are in contact with the second mating contacts. Thus, the first electrical conductor 204 of the first pneumatic component 202 is in electrical continuity with the first electrical conductor 214 of the second pneumatic component 212, and the second electrical conductor 206 of the first pneumatic component 202 is in electrical continuity with the second electrical conductor 216 of the second pneumatic component 212.

The electrical conductors and electrical identification circuits may be integrated or manufactured into the pneumatic components themselves. For instance, the electrical conductors and circuits may be formed as part of the manufacturing process of the pneumatic components. In some examples the electrical identification circuit is embedded in the pneumatic component and is not be removable. In some cases, however, a pneumatic component of a breathing circuit or pneumatic path may not have been manufactured with the electrical components and electrical identification circuit. For instance, one manufacturer of pneumatic components may include such circuitry, but another manufacturer may not. When one or more pneumatic components of the breathing circuit or pneumatic path do not include the electrical conductors and electrical identification circuit, an adapter may be used to bridge the pneumatic components that do have the requisite conductors and circuits integrated into the pneumatic components.

Figures 3, 4:
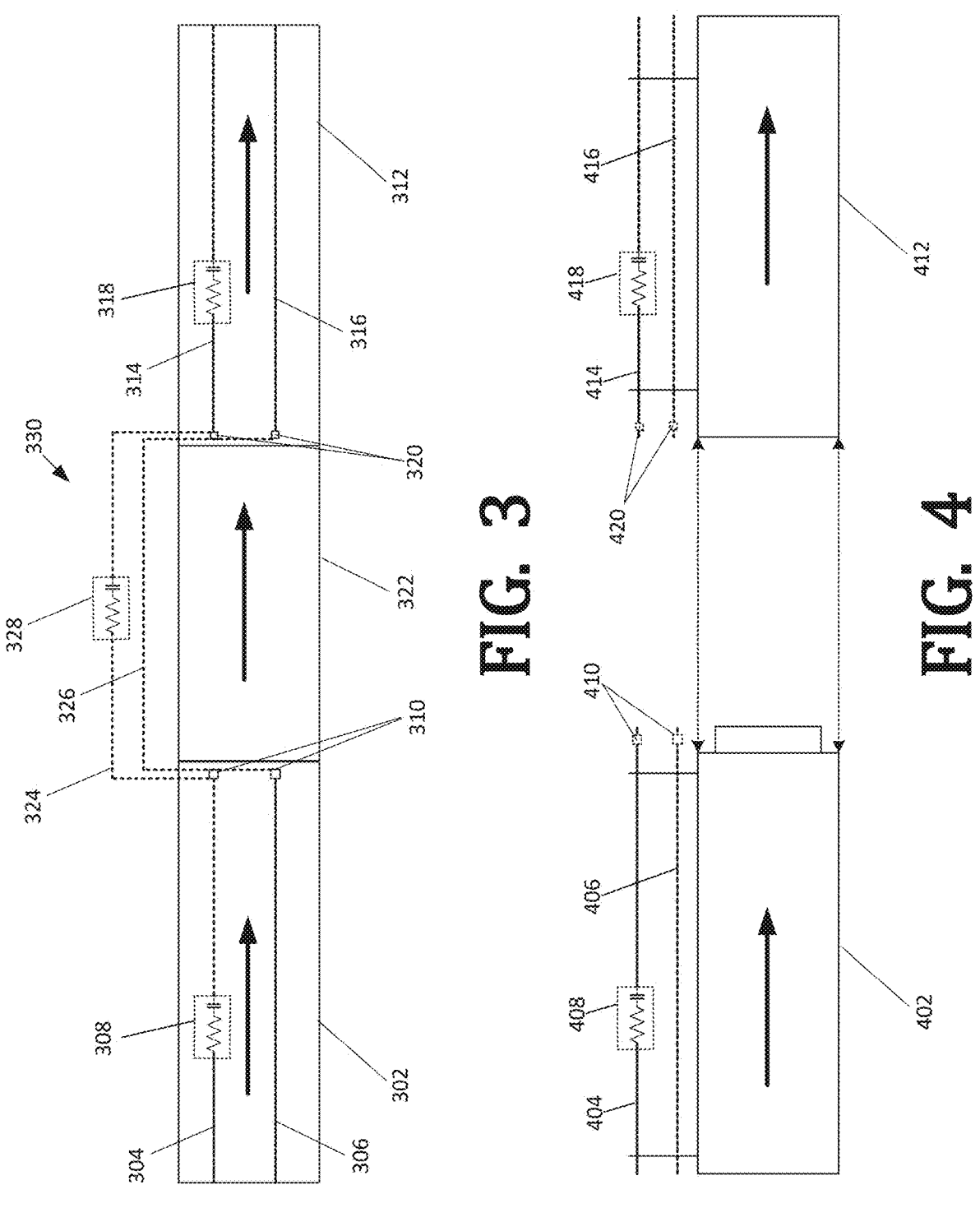
FIG. 3 is a diagram illustrating example pneumatic components and an adapter including electrical identification circuits.
FIG. 4 is a diagram illustrating example pneumatic components including external electrical identification circuits.

FIG. 3 is a diagram illustrating example pneumatic components and an adapter including electrical identification circuits. More specifically, FIG. 3 depicts a first pneumatic component 302, a second pneumatic component 312, and a third pneumatic component 322. The first pneumatic component 302 and the second pneumatic component 312 are substantially similar to the first pneumatic component 202 and the second pneumatic component 212 discussed above with reference to FIGS. 2A-2B. For instance, the first pneumatic component 302 includes a first electrical conductor 304, a second electrical conductor 306, a first electrical identification circuit 308, and first mating contacts 310. The second pneumatic component 312 includes a first electrical conductor 314, a second electrical conductor 316, a second electrical identification circuit 308, and second mating contacts 320.

The third pneumatic component 322, however, does not include the electrical contacts or an electrical identification circuit. To still be able to use the third pneumatic component 322 in the breathing circuit or pneumatic path and achieve the benefits of the present technology, an adapter 330 may be used to electrically connect the first pneumatic component 302 with the second pneumatic component 312 and identify the third pneumatic component 322 (and/or the pneumatic characteristics thereof). The adapter 330 may include a first electrical conductor 324, a second electrical conductor 326, and a third electrical identification circuit 328. When the adapter 330 is attached to the first pneumatic component 302 and the second pneumatic component 312, the first electrical conductor 324 and the second electrical conductor 326 are in contact with the respective first mating contacts 310 and the second mating contacts 320. Thus, electrical signals can be passed through the first pneumatic component 302, the adapter 330, and the second pneumatic component 312.

The third electrical identification circuit 328 of the adapter 330 may be configured to identify the third pneumatic component 322 and/or the pneumatic characteristics thereof. For instance, similar to the first electrical identification circuit 308 and the second electrical identification circuit 318, the components of the third electrical identification circuit 328 may be selected such that they identify the third pneumatic component 322 and/or the pneumatic characteristics thereof. The third electrical identification circuit 328 may be the same type of circuit (e.g., RC filter, resistor, etc.) or a different type of circuit. The third electrical identification circuit 328 may also be an integrated circuit storing data that identifies the third pneumatic component 322 and/or the pneumatic characteristics thereof. Thus, as discussed further herein, an interrogation signal may be used to determine the pneumatic characteristics of the pneumatic components even where not all the pneumatic components include integrated electrical identification circuits.

To initially determine or pre-characterize the pneumatic characteristics of the third pneumatic component 322, which may be needed to select or configure the electrical identification circuit 328, the third pneumatic component 322 may be initially pneumatically tested. The initial testing may be performed by the manufacturer and included in a datasheet or other type of database or specifications. In other examples, a third-party may test the third pneumatic component 322 to determine the pneumatic characteristics.

The adapter 330 may come in a variety of formats, including cables, wires, stickers, clips, ribbons, wireless dongles or devices (e.g., to allow short-range wireless communication over the pneumatic component), and/or other structures, that are configured to join the conductors of the adapter 330 with the mating contacts 310, 320 of the other pneumatic components 302, 312. For instance, the adapter 330 may be similar to a jumper cable with the third electrical identification circuit 328 incorporated therein. To accommodate for different types of pneumatic components, a plurality of different adapters 330 may be available with electrical identification circuits configured to match a particular pneumatic component. For example, one adapter may be manufactured to be used with a first type of humidification system and a second adapter may be manufactured to be used with a second type of humidification system. A clinician may then be able to plug in or connect the appropriate adapter when connecting the humidification system to the other pneumatic components.

FIG. 4 is a diagram illustrating example pneumatic components including external electrical identification circuits. While the electrical conductors and the electrical identification circuits discussed above have generally been discussed as being integrated into the pneumatic components, in some examples, the electrical conductors and electrical identification circuits may be external to the pneumatic components. For instance, as depicted in the FIG. 4, the first pneumatic component 402 has a first electrical conductor 404, a second electrical conductor 406, and a first electrical identification circuit 408 that are external to the first pneumatic component 402. The first electrical conductor 404 and the second electrical conductor 406 may terminate at respective mating contacts 410. The electrical components may be formed as a cable, sticker, wires, and/or other structures that are removably attachable to the first pneumatic component 402. The electrical components may be attached to the first pneumatic component 402 via means such as adhesives, clips, or other means of attachment.

Similar to the first pneumatic component 402, the second pneumatic component 412 includes a first electrical conductor 414, a second electrical conductor 416, and a second electrical identification circuit 418 that are external to the second pneumatic component 412. The first electrical conductor 414 and the second electrical conductor 416 may terminate at respective mating contacts 420. The electrical components may be formed as a cable, sticker, wires, and/or other structures that are removably attachable to the second pneumatic component 412. The electrical components may be attached to the second pneumatic component 412 via means such as adhesives, clips, or other means of attachment.

When the first pneumatic component 402 is connected to the second pneumatic component 412, the mating contacts 410 and the mating contacts 420 may come into contact with one another to allow for electrical signals to pass between the electrical conductors of the first pneumatic component 402 and the second pneumatic component 412. The mating contacts 410 and the mating contacts 420 may be formed in physical connectors that may provide a snap fit or other fit mechanism to hold the mating contacts 410 and the mating contacts 420 together.

Figure 5:
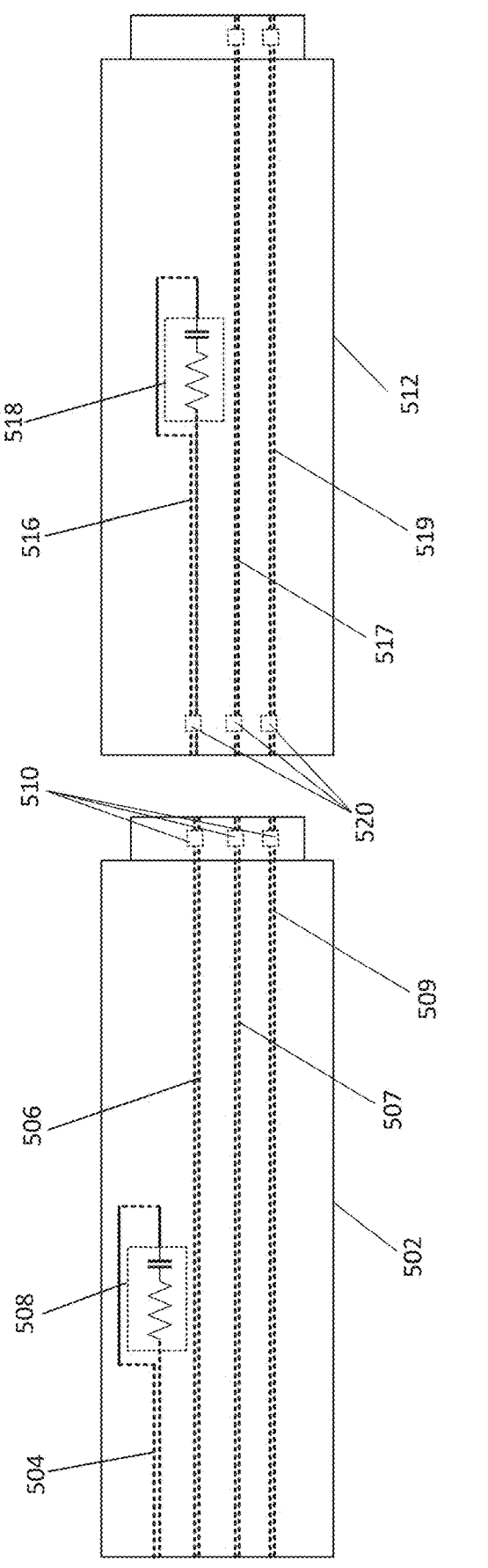
FIG. 5 is a diagram illustrating example pneumatic components including electrical identification circuits.

FIG. 5 is a diagram illustrating example pneumatic components including electrical identification circuits. More specifically, FIG. 5 depicts a first pneumatic component 502 and a second pneumatic component 512 that are to be connected to one another. The first pneumatic component 502 includes multiple pairs of electrical conductors, including a first pair of electrical conductors 504, a second pair of electrical conductors 506, a third pair of electrical conductors 507, and a fourth pair of electrical conductors 509. The first pair of electrical conductors 506, the third pair of electrical conductors 507, and the fourth pair of electrical conductors 509 terminate at respective mating contacts 510. While not shown, each of the mating contacts 510 may be split such that there is separate contact for each conductor in each pair of conductors.

The first pair of electrical conductors 504 include a first electrical identification circuit 508. Similar to the electrical identification circuits discussed above, the first electrical identification circuit 508 includes electrical components and/or an integrated circuit that may be used to identify the pneumatic characteristics of the first pneumatic component 502.

In this example, each of the pairs of conductors provides a transmission path for an interrogation signal and a return path for a response path. For example, an interrogation signal may be emitted on one of the first pair of electrical conductors 504. The interrogation signal is altered by the first electrical identification circuit 508, and a response signal is returned on other one of the first pair of electrical conductors 504. In this example, the interrogation signal is affected by only one identification circuit (i.e., the first electrical identification circuit 508). Thus, by analyzing the response signal on the first pair of electrical conductors 504, the pneumatic characteristics of the first pneumatic component 502 may be determined.

The second pneumatic component 512 also includes multiple pairs of electrical conductors, including first pair of electrical conductors 516, a second pair of electrical conductors 517, and a third pair of electrical conductors 519, which are respectively connected to mating contacts 520. While not shown, each of the mating contacts 520 may be split such that there is separate contact for each conductor in each pair of conductors. When the first pneumatic component 502 and the second pneumatic component 512 are connected, the first pair of electrical conductors 516 connects to the second pair of electrical conductors 506, the second pair of electrical conductors 517 connects to the third pair of electrical conductors 507, and the third pair of electrical conductors 519 connects to the fourth pair of electrical conductors 509.

The second pneumatic component 512 also includes a second electrical identification circuit 518. Similar to the electrical identification circuits discussed above, the second electrical identification circuit 518 includes electrical components and/or an integrated circuit that may be used to identify the pneumatic characteristics of the second pneumatic component 512. In the depicted example, an interrogation signal may be emitted on one of the second pair of electrical conductors 506 of the first pneumatic component 502, pass through to the first pair of electrical conductors 516 of the second pneumatic component 512, and be altered by the second electrical identification circuit 518 but not the first electrical identification circuit 508. Thus, by analyzing the response signal on the second pair of electrical conductors 506, the pneumatic characteristics of the second pneumatic component 512 may be determined.

Each pair of electrical conductors may be designated or used for a particular pneumatic component of the pneumatic path. For example, the first pair of electrical conductors 504 form a circuit that extends through only the first pneumatic component 502, which may be inspiratory-side ventilation tubing. The second pair of electrical conductors 506 ultimately extend through the first pneumatic component 502 and the first pair of electrical conductors 504, which may be a humidifier, an endo-tracheal tube (ETT), or some other pneumatic component. The remaining pairs of electrical conductors may ultimately reach electrical identification circuits of specific pneumatic components, such as a wye or an endotracheal tube. Thus, where different pairs of conductors may be used to automatically determine pneumatic characteristics of different pneumatic components of the pneumatic path.

FIG. 6A depicts an example lookup table for conversion of electrical characteristics to pneumatic characteristics. As discussed above, the electrical identification circuits may be connected in series with one another throughout the pneumatic path such that an interrogation signal is altered by the electrical identification circuits to form a response signal, which is detected and analyzed. Based on the response signal, the aggregate electrical characteristics of the electrical identification circuits may be determined. For example, an aggregate electrical impedance for the combined electrical identification circuits may be determined. A lookup table, such as the lookup table in FIG. 6A, may then be used to determine the pneumatic characteristics of the pneumatic path. For instance, if the aggregate impedance has a value of Z1, the pneumatic path has a pneumatic resistance of PR1 and a pneumatic compliance of PC1. Similarly, if the aggregate impedance has a value of Z2, the pneumatic path has a pneumatic resistance of PR2 and a pneumatic compliance of PC2.

FIG. 6B depicts an example lookup table for conversion of electrical characteristics to pneumatic characteristics. As discussed above, the measured electrical characteristic(s), such as impedance, may be used to identify a pneumatic component and/or a unique combination of pneumatic components. Based on the identification of the pneumatic component(s), a subsequent lookup or query may be executed to find the pneumatic characteristic(s) of the pneumatic component(s). For instance, as shown in FIG. 6B, if the impedance has a value of Z1, the pneumatic path includes a pneumatic component or unique combination of pneumatic components having a pneumatic identifier (ID) of PID1. Similarly, if the impedance has a value of Z2, the pneumatic path includes a pneumatic component or unique combination of pneumatic components having a pneumatic identifier (ID) of PID2. The pneumatic identifiers may explicitly indicate each type of pneumatic component in the unique combination and/or a single pneumatic component. For instance, the supplier or manufacturer of the pneumatic component(s) may be indicated. In other examples, the pneumatic identifiers may be used to query a database to determine the corresponding pneumatic components associated with a respective pneumatic identifier.

FIG. 7 depicts another example lookup table for conversion of electrical characteristics to pneumatic characteristics. In some examples, multiple aggregate electrical characteristics may be determined for the combined electrical identification circuits in the breathing circuit or pneumatic path. For instance, an aggregate electrical resistance and an aggregate electrical capacitance may be determined. Each of those electrical characteristics may be correlated with one or more pneumatic characteristics of the pneumatic path. In the lookup table depicted in FIG. 7, the first aggregate electrical characteristic may be electrical resistance and the second aggregate electrical characteristic may be electrical capacitance. Based on the aggregate electrical resistance, a corresponding pneumatic resistance may be determined from the table. For instance, if the aggregate electrical resistance has a value of R1, the pneumatic path has a pneumatic resistance of PR1. Based on the aggregate electrical capacitance, a corresponding pneumatic resistance may also be determined from the table. For instance, if the aggregate electrical capacitance has a value of C1, the pneumatic path has a pneumatic resistance of PC1.

The lookup tables, such as those depicted in FIGS. 6-7, may be generated based on unique combinations of pneumatic components of the pneumatic path and the known pneumatic characteristics of those pneumatic components. For instance, the electrical components selected for the electrical identification circuits may be selected such that most, if not all, possible unique combinations of pneumatic components in a pneumatic path result in a different aggregate electrical characteristic (e.g., a different row of the lookup table). Accordingly, the aggregate electrical characteristic may be used to identify the unique combination of pneumatic components and the total pneumatic characteristics for the pneumatic path including that combination of pneumatic components.

In other examples, rather than using a lookup table, the pneumatic characteristics may be represented as a function of the electrical characteristic. For instance, the pneumatic resistance may be represented as a function of the electrical resistance. Thus, once the electrical resistance is measured or determined, the pneumatic resistance may be determined using the function. Other combinations of pneumatic characteristics and electrical characteristics may be used.

Figure 8A:
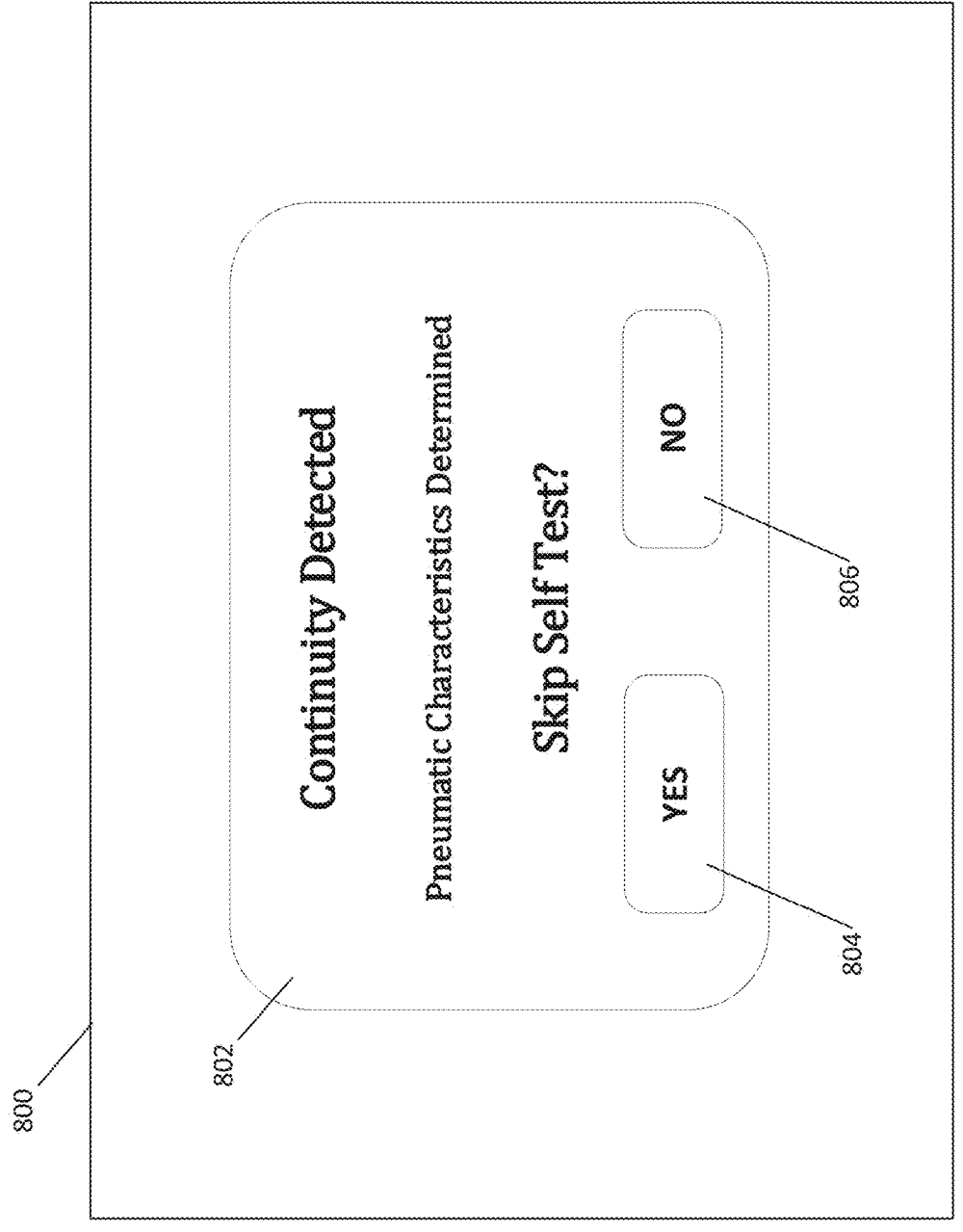
FIG. 8A depicts an example user interface displayed on a display of a ventilator.
Figure 8B:
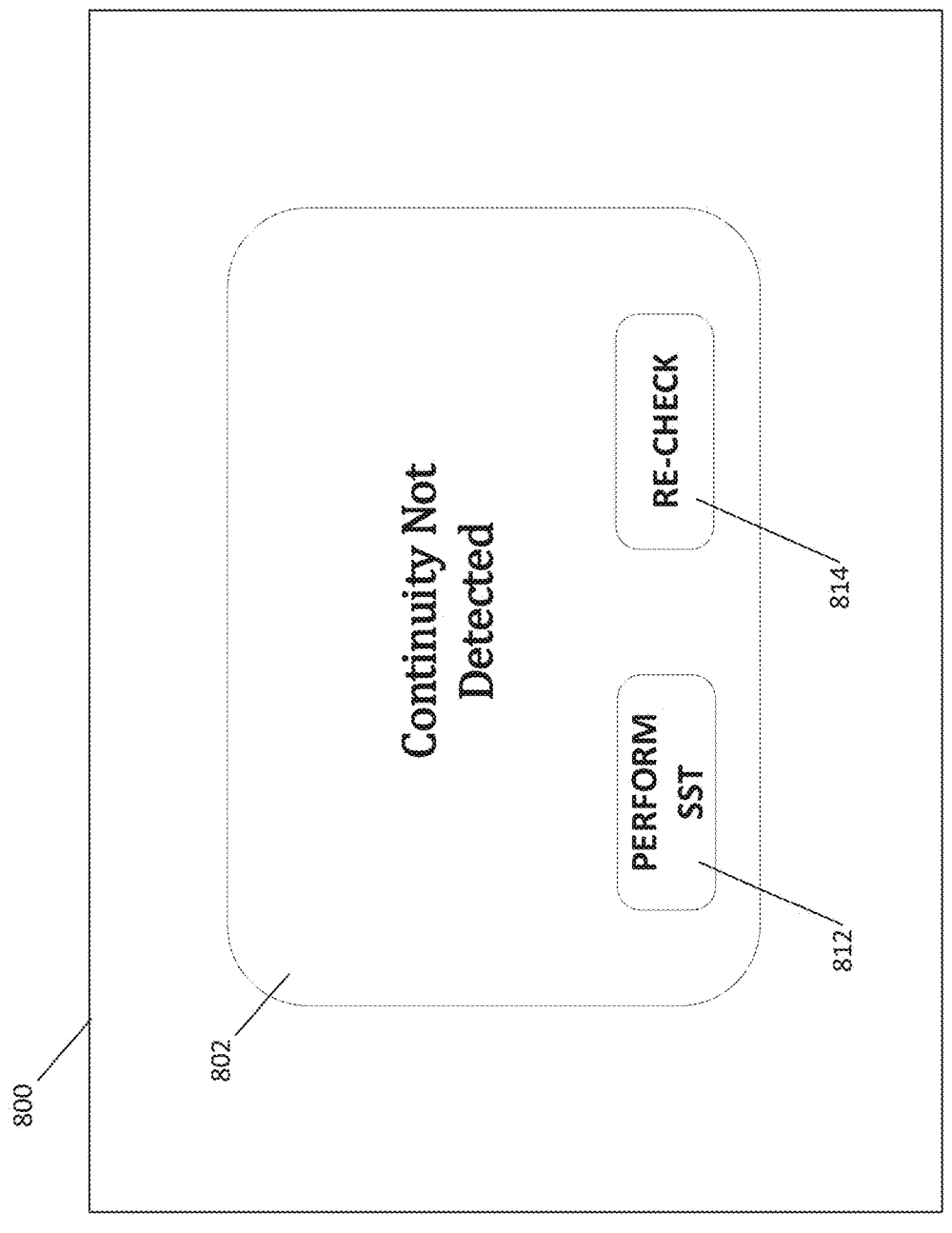
FIG. 8B depicts another example user interface displayed on a display of a ventilator.

FIGS. 8A-8B depict an example user interface displayed on a display 800 of a ventilator. The example user interface includes a continuity interface element 802, which may be a window or other displayed segment. The continuity interface element 802 indicates whether continuity of the pneumatic path has been detected. As discussed above, based on an electric signal being able to pass through the electrical conductors of the pneumatic components of the pneumatic path, continuity of the pneumatic path (e.g., the pneumatic components of the pneumatic path are physically connected) may be determined. Accordingly, upon startup of the ventilator or another trigger (such as selection of a continuity check option), continuity of the pneumatic path may be checked using an electrical signal (e.g., a continuity signal or an interrogation signal).

If continuity is detected, the continuity interface element 802 indicates that continuity of the pneumatic path has been detected, as shown in FIG. 8A. Additionally or alternatively, the continuity interface element 802 may indicate whether the pneumatic characteristics of the pneumatic path were able to be determined. In the example in FIG. 8A, the pneumatic characteristics were able to be determined, and the continuity interface element 802 indicates the same. In some examples, the values of the pneumatic characteristics may also be displayed in the continuity interface element 802 or in another area on the display 800.

In addition, based on the pneumatic characteristics and/or the identification of the pneumatic components, the present technology may determine whether the pneumatic components are appropriate for the patient type being ventilated. For instance, if the pneumatic characteristics or identification indicate the pneumatic components are adult components and the patient being ventilated is pediatric or neonatal (which may be provided as an input to the ventilator), the pneumatic components may be determined to be potentially inappropriate or incorrect. If the pneumatic components are determined to be potentially inappropriate for the patient, a confirmation or warning may be displayed indicating that the pneumatic components may be incorrect.

Where continuity is detected and/or the pneumatic characteristics are determined from the interrogation signal and corresponding response signal, the traditional self start test (or portions thereof) may be skipped. For example, portions of the self-start test (SST) that would have been needed to determine the pneumatic characteristics may be skipped or omitted. Options to skip the self-start test may be presented in the continuity interface element 802. In the example depicted, a "yes" selectable element 804 and a "no" selectable element 806 may be presented for user selection regarding whether the SST should be skipped. In other examples, the SST may be automatically skipped, or a shortened or abbreviated SST or circuit check may be performed, when continuity and/or the pneumatic characteristics are determined from the electrical signals.

If continuity is not detected, the continuity interface element 802 indicates that continuity of the pneumatic path has not been detected, as shown in FIG. 8B. Continuity may not be detected where the pneumatic components of the pneumatic path are not properly physically connected to one another. In other examples, continuity may not be detected where one or more of the pneumatic components do not include the electrical conductors of the present technology and no adapters have been used. Thus, when a clinician is prompted with a continuity interface element 802 indicating continuity is not detected, the clinician can inspect the pneumatic path to connect the pneumatic components properly and/or attach any adapters for pneumatic components that do not include the electrical conductors of the present technology. In some examples, when continuity is not detected, an SST or circuit check may be automatically performed without an additional alert or prompt. The continuity interface element 802 may then be based on the results of the SST or circuit check and electrical continuity test.

Two options may be presented in the continuity interface element 802 where continuity is not detected. A first option may be a Perform SST selectable element 812. Upon receipt of a selection of the Perform SST selectable element, the ventilator may perform a traditional SST to determine the pneumatic characteristics of the pneumatic path. Such an option may be selected when the clinician is aware that at least one pneumatic component does not include the electrical conductors of the present technology and the clinician does not want to attach an adapter. A second option may be a Re-Check selectable element 814. Upon receipt of a selection of the Re-Check selectable element 814, the ventilator may re-check for continuity of the pneumatic path using electrical signals as discussed herein. A clinician may select the re-check selectable element 814 when the clinician has checked the pneumatic path for physical disconnects and/or added any adapters to the pneumatic path.

Figure 9:
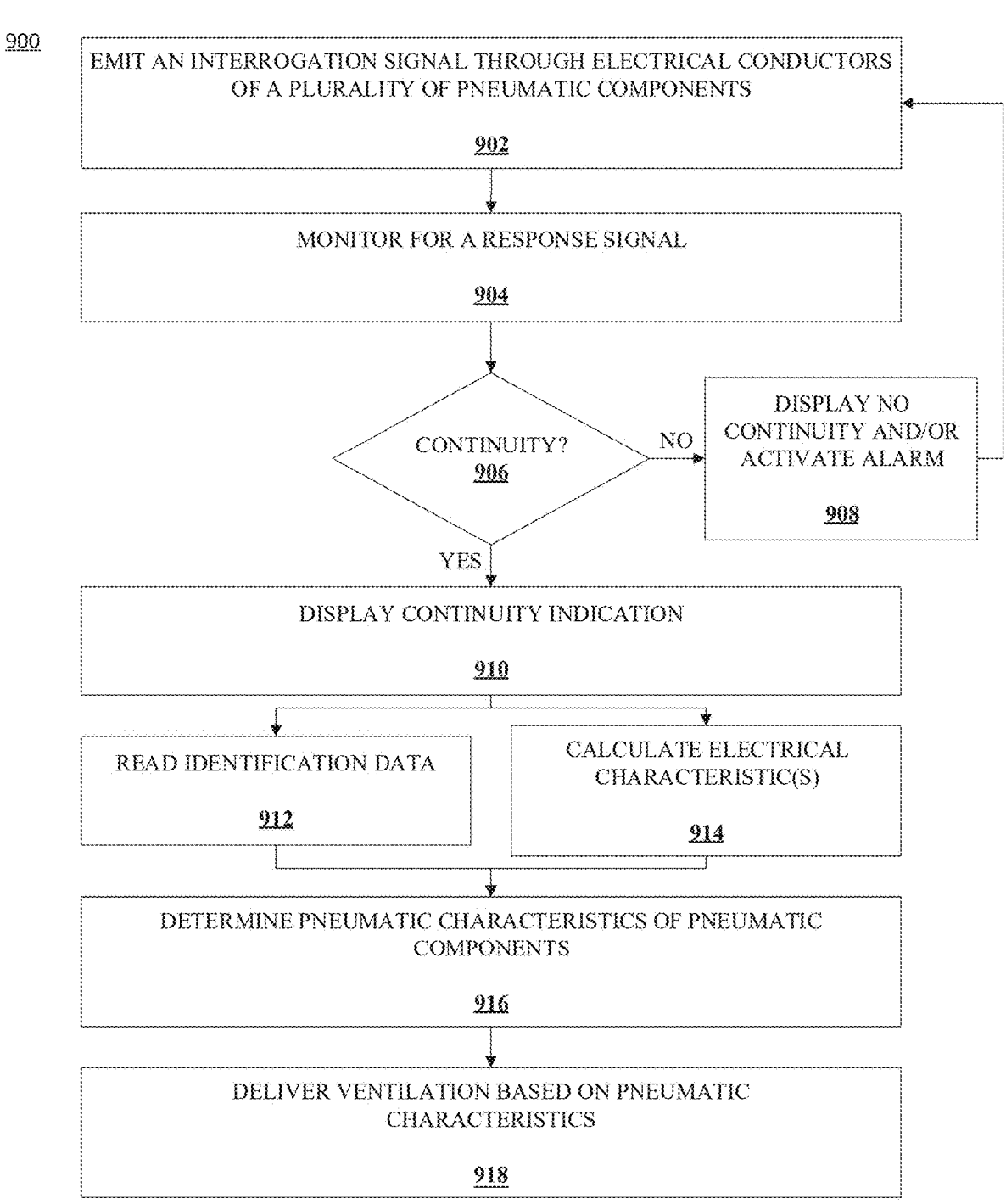
FIG. 9 depicts an example method for automatically characterizing pneumatic components of a breathing circuit.

FIG. 9 depicts an example method 900 for automatically characterizing pneumatic components of a pneumatic path. The operations of method 900 may be performed by a ventilator, or one or more components thereof, to which the pneumatic path is connected. At operation 902, an interrogation signal is emitted through electrical conductors of a plurality of pneumatic components of a pneumatic path of a ventilator. For instance, the interrogation signal is emitted on an electrical conductor of a first pneumatic component and the interrogation signal travels to an electrical conductor of a second pneumatic component. The interrogation signal may be emitted from a particular portion of the ventilator. For example, the interrogation signal may be emitted at the inspiratory port and/or expiratory port of the ventilator.

As discussed above, the interrogation signal may take different forms. For instance, the interrogation signal may be a simple DC voltage or may be a time series of different frequencies, among other types of signals. In examples where the electrical identification circuits include microchips or integrated circuits storing identification data about the respective pneumatic component, the interrogation signal may be a specific signal configured to cause the microchip or integrated circuit to return the identification data. For instance, each electrical identification circuit may be separately addressable such that the interrogation signal includes the address(es) of the electrical identification circuits and a corresponding request for the identification data. The interrogation signal may thus include multiple requests, each request with a different address. The response signal may then include identification data including the address (or some other identifier) of the electrical identification circuit from which the identification data originated. In any case, the response signal may interact with and/or be altered by the electrical identification circuits of the pneumatic components.

At operation 904, monitoring for a response signal is performed. The response signal may be the identification data where the electrical identification circuits are integrated circuits storing such data. In examples where the electrical identification circuits are not such type of integrated circuits, the response signal is the interrogation signal after the interrogation signal has been altered by the electrical identification circuits in the electrical path on which the interrogation signal travels. Monitoring for a response signal may include having a signal reader in an active mode for a period of time. In some cases where continuity is checked at intervals or continuously checked, monitoring for the response signal may occur over an extended period of time.

The response signal may be received at a particular portion of the ventilator. For example, if the interrogation signal is emitted at the inspiratory port, the response signal may be detected at the expiratory port. Similarly, if the interrogation is emitted at the expiratory port, the response signal may be detected at the inspiratory port. In other examples where portions of the pneumatic path are being separately analyzed, the response signal may be detected at the same location of ventilator from which the interrogation signal is emitted. For instance, the pneumatic components may include an electrical conductor for a transmission path and an electrical conductor for a return path. In such examples, the inspiratory side of a pneumatic path may be analyzed, and the path between the transmission path and the return path may be completed in a particular pneumatic component, such an endotracheal tube or a wye. The expiratory side of the pneumatic path may be similarly analyzed, and another interrogation signal may be emitted at the expiratory port and the corresponding response signal detected at the expiratory port.

At operation 906, continuity of the pneumatic path (or a portion of the pneumatic path including the pneumatic components through which the interrogation signal passed) is determined. If a response signal is detected when monitoring for the response signal in operation 904, continuity may be determined at operation 906 because the interrogation signal was able to pass through the electrical conductors of the pneumatic path or analyzed portion of the pneumatic path. If an absence of a response signal is detected (e.g., no response signal is detected), a lack of continuity is determined at operation 906 because the interrogation signal was not able to pass through the pneumatic path or analyzed portion thereof.

Where a lack of continuity is detected or determined at operation 906, an indication of no continuity may be displayed and/or a disconnect alarm may be activated at operation 908. For example, when the lack of continuity is identified at startup or initialization, the continuity interface element of FIG. 8B may be displayed. If a lack of continuity is detected (after continuity being previously detected) while a patient is being ventilated, a disconnect alarm or indication may be announced, sounded, and/or displayed to indicate that the pneumatic path has become disconnected. Additional changes in ventilation may be made by the ventilator based on the detection of the disconnect. From operation 908, method 900 may flow back to operation 902 where the method repeats and continuity is checked again. The method may flow from operation 902 to operation 908 automatically or upon receiving a selected option, such as a selection of the Re-Check selectable element.

Where continuity is detected or determined in operation 910, the method 900 flows to operation 910 where a continuity indication may be displayed. For example, the continuity interface element of FIG. 8A may be displayed. Additionally or alternatively, an icon or other indicator on the ventilator may change to indicate whether continuity is detected. Such an icon or indicator may change form depending on the continuity determination.

Operation 912 or operation 914 may be performed depending on the configuration of the electrical identification circuits in the pneumatic components. In examples where the electrical identification circuits in the pneumatic components are integrated circuits storing identification data, that identification data is read at operation 912. As discussed above, the identification data may include an identification of the type of pneumatic component (e.g., make/model of the pneumatic component) and/or the pneumatic characteristics themselves.

In examples where the electrical identification circuits are not integrated circuits storing identification data, operation 914 is performed to calculate one or more electrical characteristics of the electrical identification circuits. The electrical characteristics may be the aggregate electrical characteristics discussed above. The electrical characteristics may be determined based on analysis of the response signal as compared to the interrogation signal. For instance, the current and/or voltage change of the interrogation signal caused by the electrical identification circuits may be determined based on analysis of the response signal. Electrical characteristics, such as electrical resistance, capacitance, inductance, and/or impedance, may be determined or calculated from such an analysis.

At operation 916, one or more pneumatic characteristics of the pneumatic components through which the interrogation signal passed are determined. In examples where identification data is read in operation 912, the pneumatic characteristics may be determined based on the identification. Where the identification data includes the pneumatic characteristics, determining the pneumatic characteristics includes combining the pneumatic characteristics for each of the pneumatic components to determine the overall pneumatic characteristics of the pneumatic path or the portion of the pneumatic path analyzed. Where the identification data includes identifiers of an identification of the type of pneumatic component (e.g., make/model of the pneumatic component), the types of pneumatic components may be queried (e.g., perform a lookup operation), and the response to the query includes the pneumatic characteristics for the queried pneumatic components. The received pneumatic characteristics may then be summed or combined to determine the pneumatic characteristics of the pneumatic path or analyzed portion of the pneumatic path. In some examples, operation 916 includes determining the aggregate pneumatic characteristics of the pneumatic path and/or the portion of pneumatic path analyzed.

In examples, where the one or more electrical characteristics are calculated or determined in operation 914, the pneumatic characteristics may be determined through the use of a lookup operation or query of a lookup table, such as the lookup tables depicted in FIGS. 6-7 and discussed above. For instance, the lookup table may be queried with the calculated electrical characteristic(s). Alternatively, the pneumatic characteristics may be determined from a function where pneumatic characteristic(s) are a function of the electrical characteristic(s).

At operation 918, ventilation is delivered based on the pneumatic characteristics for the pneumatic path, or portion of the pneumatic path, determined in operation 916. For example, the flow, volume, and/or pressure delivery of the ventilator may be set, altered, compensated, and/or corrected based on the pneumatic characteristics. Where the method 900 is initiated at ventilator startup, operation 918 may include the initialization or correction/compensation to be used by the ventilator. Ventilation (e.g., breathing gases) is then delivered to the patient based on the altered or compensated ventilation targets according to the ventilation settings for the patient. For instance, a ventilation parameter such as flow, pressure, or volume, may be adjusted based on the pneumatic characteristics such that the adjusted ventilation parameters achieve the ventilation settings (e.g., the settings provided by the clinician for the ventilated patient).

The method 900 may then repeat to continue checking for continuity. The method 900 may repeat automatically, or upon a trigger, such as a change to the breathing circuit or receipt of a selection of option to re-check the breathing circuit.

Figure 10:
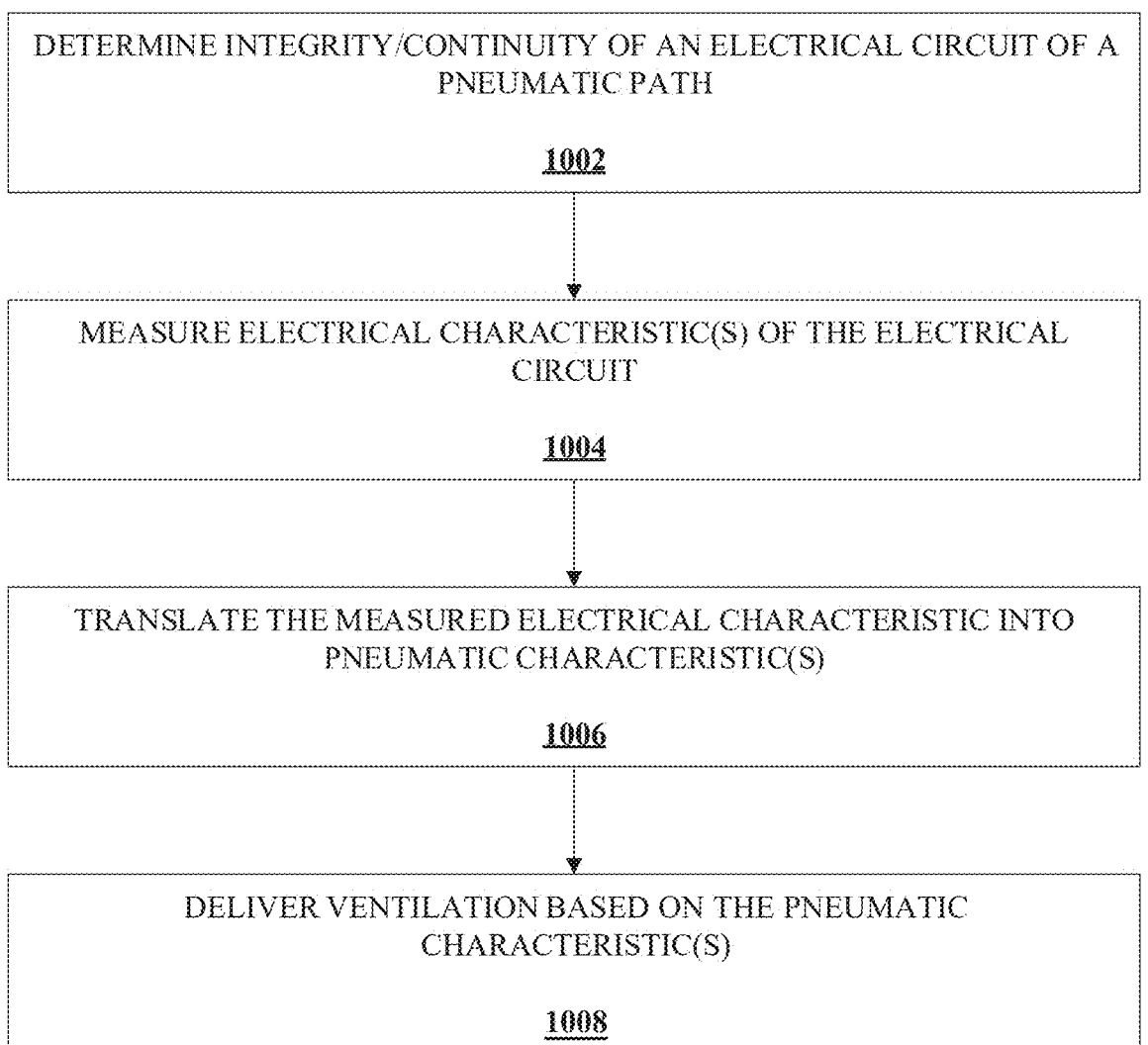
FIG. 10 depicts another example method for delivering ventilation.

FIG. 10 depicts another example method 1000 for delivering ventilation. Method 1000 may occur at ventilation startup and/or in lieu of an SST, as discussed above. At operation 1002, the integrity and/or continuity of an electrical circuit of a pneumatic path may be determined. Such a determination may be made using any of the techniques discussed herein, such as emitting a signal and analyzing a response to that signal (or an absence of a response signal.) At operation 1004, if continuity/integrity is detected/determined at operation 1002, one or more electrical characteristics of the electrical circuit are measured or otherwise calculated. The electrical characteristic(s) may be calculated or measured from the response signal detected in operation 1002. In other examples, the electrical characteristic(s) may be measured using separate or subsequent electrical measurement techniques. At operation 1006, the electrical characteristic(s) that are measured or calculated in operation 1004 are translated or converted to one or more pneumatic characteristics. Translating/converting the electrical characteristic(s) to pneumatic characteristic(s) may be achieved through any of the techniques discussed herein, such as the use of lookup tables. At operation 1008, ventilation is delivered that is adjusted or compensated based on the determine pneumatic characteristics. For instance, the delivery of ventilation may be compensated based on the determined pneumatic characteristics to achieve ventilation targets according to ventilation settings for the patient. In some examples, the ventilation settings may be adjusted or set based on the determined pneumatic components. The pneumatic characteristics and/or the identified pneumatic components may also be stored in a log or data file to track which types of pneumatic components have been attached and, in some cases, when those pneumatic components were attached.

Figure 11:
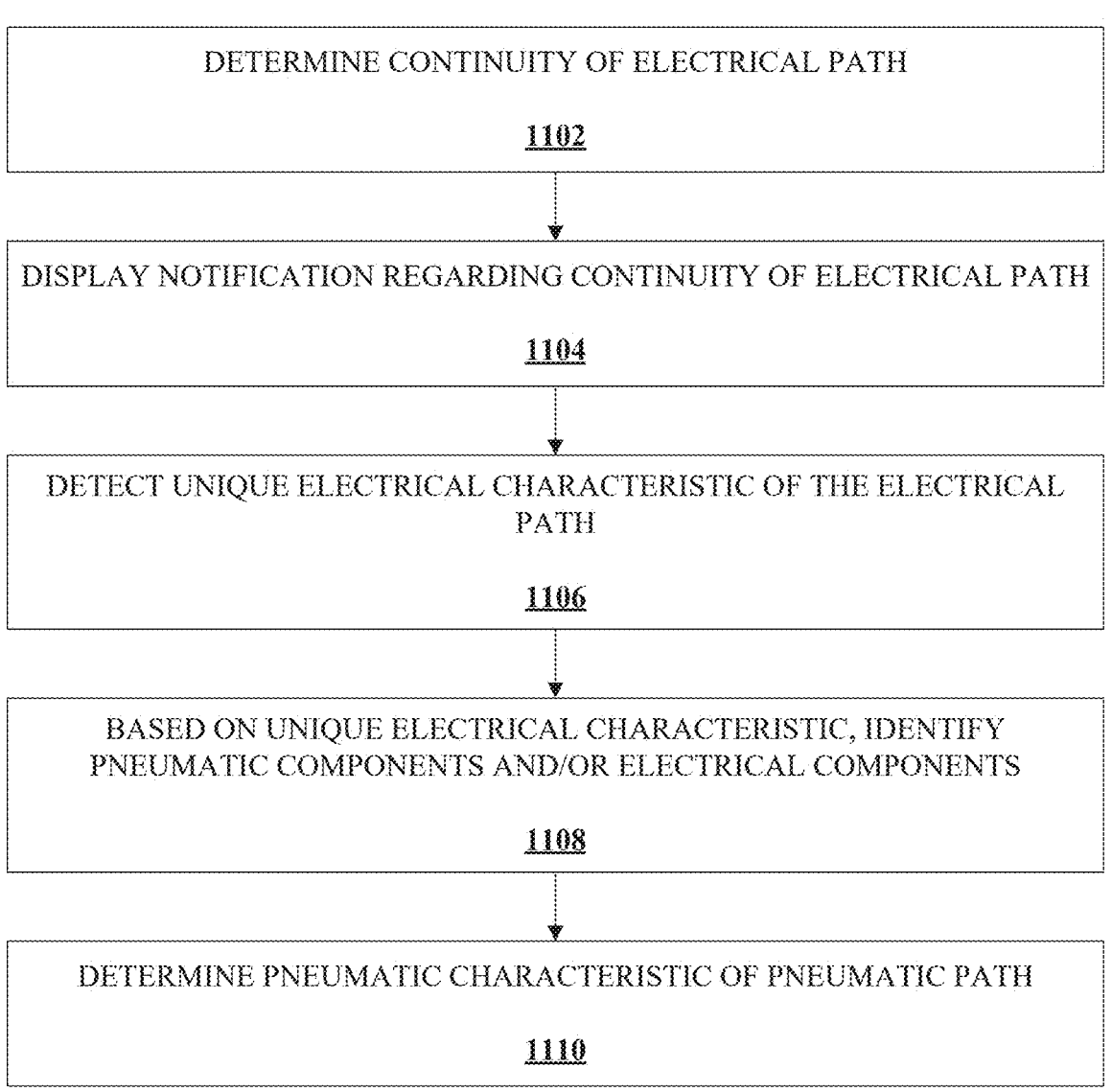
FIG. 11 depicts another example method for identifying pneumatic characteristics of pneumatic components.

FIG. 11 depicts another example method 1100 for identifying pneumatic characteristics of pneumatic components. At operation 1102, continuity of an electrical path is determined. The electrical path is formed by electrical conductors and electrical components of pneumatic components of the pneumatic path. For instance, pneumatic path may include a first pneumatic component and a second pneumatic component. The first pneumatic component may include a conductor (e.g., a wire) and a first electrical component, and the second pneumatic component may include a conductor (e.g., a wire) and second electrical component. When the first pneumatic component and the second pneumatic component are connected to one another, the conductors of the pneumatic components may also connect forming an electrical path that includes the first electrical component and the second electrical component. The continuity of the electrical path may be determined in any of the manners discussed herein, such as emitting an interrogation signal and detecting a response signal. Other manners of detecting continuity of an electrical path or circuit may also be utilized.

At operation 1104, a notification regarding the determined continuity of the electrical path is displayed. For instance, if continuity is determined, a notification may be displayed indicating that such continuity has been detected. In con-trast, if continuity is not detected, a notification may be displayed indicating that continuity has not been detected. In some examples, the notification may be displayed in the form of one of the user interfaces discussed above and depicted in FIGS. 8A-8B.

At operation 1106 a unique electrical characteristic of the electrical path is detected. The unique characteristic of the electrical path may be an electrical characteristic based on the electrical components that are included in the electrical path. For instance, using the example above where two pneumatic components are connected, the unique electrical characteristic of the pneumatic path may be a combination of, or at least based on, the first electrical characteristic and the second electrical characteristic.

At operation 1108, based on the unique electrical characteristic detected in operation 1106, the pneumatic components may be identified and/or the electrical components in the electrical path may be identified. For instance, a lookup table may be used to identify the pneumatic components, among other possible ways discussed herein to identify the pneumatic components. The individual electrical components may also (or alternatively) be identified. For instance, from the unique electrical characteristic, the individual electrical components (e.g., the first and second electrical components) may be identified.

At operation 1110, one or more pneumatic characteristics of the pneumatic path are determined based on the identification(s) made in operation 1108. Ventilation parameters and/or settings may then be adjusted to deliver ventilation that compensates for the determined pneumatic characteristic(s).

Those skilled in the art will recognize that the methods and systems of the present disclosure may be implemented in many manners and as such are not to be limited by the foregoing aspects and examples. In other words, functional elements being performed by a single component, or multiple components, in various combinations of hardware and software or firmware, and individual functions, can be distributed among software applications at either the client or server level or both. In this regard, any number of the features of the different aspects described herein may be combined into single or multiple aspects, and alternate aspects having fewer than or more than all of the features herein described are possible.

Functionality may also be, in whole or in part, distributed among multiple components, in manners now known or to become known. Thus, a myriad of software/hardware/firmware combinations are possible in achieving the functions, features, interfaces, and preferences described herein. Moreover, the scope of the present disclosure covers conventionally known manners for carrying out the described features and functions and interfaces, and those variations and modifications that may be made to the hardware or software firmware components described herein as would be understood by those skilled in the art now and hereafter. In addition, some aspects of the present disclosure are described above with reference to block diagrams and/or operational illustrations of systems and methods according to aspects of this disclosure. The functions, operations, and/or acts noted in the blocks may occur out of the order that is shown in any respective flowchart. For example, two blocks shown in succession may in fact be executed or performed substantially concurrently or in reverse order, depending on the functionality and implementation involved.

Further, as used herein and in the claims, the phrase "at least one of element A, element B, or element C" is intended to convey any of: element A, element B, element C, elements A and B, elements A and C, elements B and C, and elements A, B, and C. In addition, one having skill in the art will understand the degree to which terms such as "about" or "substantially" convey in light of the measurement techniques utilized herein. To the extent such terms may not be clearly defined or understood by one having skill in the art, the term "about" shall mean plus or minus ten percent.

Numerous other changes may be made which will readily suggest themselves to those skilled in the art and which are encompassed in the spirit of the disclosure and as defined in the appended claims. While various aspects have been described for purposes of this disclosure, various changes and modifications may be made which are well within the scope of the disclosure. Numerous other changes may be made which will readily suggest themselves to those skilled in the art and which are encompassed in the spirit of the disclosure and as defined in the claims.

What is claimed is:

1. A ventilation system comprising:
a pressure source;
a pneumatic path configured to receive gas from the pressure source and comprising a first pneumatic component coupled to a second pneumatic component, wherein:
the first pneumatic component comprises a first electrical conductor including a first electrical component having a first electrical characteristic, and
the second pneumatic component comprises a second electrical conductor including a second electrical component having a second electrical characteristic different than the first electrical characteristic, wherein the first electrical conductor is electrically connected with the second electrical conductor in an electric path and wherein the first and second electrical characteristics produce a unique electrical characteristic of the electric path;
a processor; and
memory storing instructions that, when executed by the processor, causes the ventilation system to perform operations comprising:
determining a continuity of the electrical path;
displaying a notification regarding the continuity of the electrical path;
emitting, through the electrical path, an interrogation signal that includes a time series of different frequencies;
detecting a response signal that includes a response to different frequencies of the interrogation signal;
based on the response signal, identifying at least one of the first and second pneumatic components or the first and second electrical components; and
based on the identifying, determining a pneumatic characteristic of the pneumatic path.

2. The system of claim 1, wherein the pneumatic characteristic includes at least one of airway resistance and airway compliance.

3. The system of claim 1, wherein the pneumatic characteristic includes at least one of a gas volume or gas flow alteration caused by the at least one of the first pneumatic component or the second pneumatic component.

4. The system of claim 1, wherein:
the first pneumatic component is one of a breathing circuit, an inspiratory filter, an expiratory filter, a humidification system, a wye, a flow sensor, an endotracheal tube, a nasal cannula, a mask, a suction catheter, a water trap, a nebulizer, or a percussor; and the second pneumatic component is one of a breathing circuit, an inspiratory filter, an expiratory filter, a humidification system, a wye, a flow sensor, an endotracheal tube, a nasal cannula, a mask, a suction catheter, a water trap, a nebulizer, or a percussor.

5. The system of claim 1, wherein the operations further comprise:
adjusting a ventilation parameter according to the pneumatic characteristic, wherein the ventilation parameter is at least one of flow, pressure, volume; and
delivering ventilation according to the adjusted ventilation parameters.

6. The system of claim 1, wherein the response signal includes a first identifier for the first pneumatic component and a second identifier for the second pneumatic component, and determining the pneumatic characteristic includes performing a lookup operation to identify the pneumatic characteristic.

7. The system of claim 1, wherein the first electrical conductor including the first electrical component is removable from the first pneumatic component.

8. The system of claim 1, further comprising:
a third pneumatic component; and
an adapter comprising a third electrical conductor including a third electrical component corresponding to the third pneumatic component, the adapter coupling the third pneumatic component with at least one of the first pneumatic component or the second pneumatic component.

9. A method for automatically characterizing pneumatic components of a pneumatic path for a ventilator, the method comprising:
emitting an interrogation signal through electrical conductors of a plurality of pneumatic components of the pneumatic path;
detecting a response signal from the electrical conductors of the plurality of pneumatic components of the pneumatic path;
based on the response signal, determining an aggregate electrical characteristic; and
based on the aggregate electrical characteristic, determining at least one of:
an identity of a unique combination of the plurality of pneumatic components; or
one or more pneumatic characteristics of the pneumatic path.

10. The method of claim 9, further comprising:
performing an abbreviated circuit check based on the identity of the unique combination or the one or more pneumatic characteristics.

11. The method of claim 9, wherein the identity of the unique combination of the plurality of pneumatic components is determined.

12. The method of claim 9, wherein the one or more pneumatic characteristics of the pneumatic path are determined.

13. The method of claim 12, wherein:
the aggregate electrical characteristic is at least one of electrical impedance, electrical resistance, electrical capacitance, or electrical inductance.

14. A method, performed by a ventilator, for automatically characterizing pneumatic components of a pneumatic path, the method comprising:
emitting an interrogation signal through electrical conductors of a first pneumatic component and a second pneumatic component of a pneumatic path, wherein the interrogation signal includes a time series of different frequencies and the interrogation signal is altered by a first electrical identification circuit of the first pneumatic component and a second identification circuit of the second pneumatic component;

receiving a response signal in response to the interrogation signal, wherein the response signal includes a response to different frequencies of the interrogation signal;

based on the response signal, determining at least one pneumatic characteristic of the first pneumatic component and the second pneumatic component; and delivering ventilation that is compensated based on the pneumatic characteristics.

15. The method of claim 14, the method further comprising:

determining an electrical characteristic of the first electrical identification circuit, wherein the electrical characteristic is at least one of electrical impedance, electrical resistance, electrical capacitance, or electrical inductance; and wherein the at least one pneumatic characteristic is determined based on the electrical characteristic.

16. The method of claim 14, wherein the response signal includes a first identifier for the first pneumatic component and a second identifier for the second pneumatic component, and determining the at least one pneumatic characteristic includes performing a lookup operation to identify the at least one pneumatic characteristic.

\* \* \* \* \*